US011672739B2

(12) United States Patent
Shibata

(10) Patent No.: US 11,672,739 B2
(45) Date of Patent: Jun. 13, 2023

(54) MEDICATION DISPENSING DEVICE, CONTROL METHOD, AND CONTROL PROGRAM

(71) Applicant: YUYAMA MFG. CO., LTD., Osaka (JP)

(72) Inventor: Tomoyuki Shibata, Osaka (JP)

(73) Assignee: YUYAMA MFG. CO., LTD., Osaka (JP)

( * ) Notice: Subject to any disclaimer, the term of this patent is extended or adjusted under 35 U.S.C. 154(b) by 724 days.

(21) Appl. No.: 16/613,803

(22) PCT Filed: Mar. 4, 2019

(86) PCT No.: PCT/JP2019/008344
§ 371 (c)(1),
(2) Date: Nov. 15, 2019

(87) PCT Pub. No.: WO2019/172173
PCT Pub. Date: Sep. 12, 2019

(65) Prior Publication Data
US 2020/0170887 A1    Jun. 4, 2020

(30) Foreign Application Priority Data

Mar. 5, 2018  (JP) .............................. JP2018-038587

(51) Int. Cl.
*A61J 7/00* (2006.01)
*G16H 20/13* (2018.01)
(Continued)

(52) U.S. Cl.
CPC ............... *A61J 7/0084* (2013.01); *A61J 1/03* (2013.01); *G07F 17/0092* (2013.01); *G16H 20/13* (2018.01); *A61J 2200/30* (2013.01)

(58) Field of Classification Search
CPC ........ A61J 1/03; A61J 7/0084; A61J 2200/30; G07F 17/0092; G16H 20/13
See application file for complete search history.

(56) References Cited

U.S. PATENT DOCUMENTS

2006/0266763 A1* 11/2006 Svabo Bech ....... G07F 17/0092
221/83
2007/0179957 A1* 8/2007 Gibson .................. G16H 70/40
(Continued)

FOREIGN PATENT DOCUMENTS

CN          104379110 A      2/2015
EP          2853252 A1 *     4/2015  ................ A61J 3/00
(Continued)

OTHER PUBLICATIONS

Office Action in CN Application No. 201980002434.6, dated Dec. 30, 2021. 12pp .

(Continued)

*Primary Examiner* — Rafael A Ortiz
(74) *Attorney, Agent, or Firm* — Hauptman Ham, LLP

(57) ABSTRACT

A drug dispensing device includes: a variable cassette configured to dispense any type of drug; a mounting portion, to and from which the variable cassette is mountable and dismountable; a drive controller configured to cause the drug corresponding to the plurality of pieces of prescription data to be dispensed from the set; an allocation processor configured to allocate, based on the plurality of pieces of prescription data, drug information on the drug to be dispensed included in the plurality of pieces of prescription data to the variable cassette or the mounting portion; and a drive controller configured to drive the variable cassette in accordance with a driving condition set in advance in association with the drug information allocated to the variable cassette or the mounting portion by the allocation (Continued)

processor, to thereby dispense from the variable cassette the drug corresponding to the plurality of pieces of prescription data.

8 Claims, 14 Drawing Sheets

(51) Int. Cl.
*A61J 1/03* (2023.01)
*G07F 17/00* (2006.01)

(56) References Cited

U.S. PATENT DOCUMENTS

| | | |
|---|---|---|
| 2012/0216485 A1 | 8/2012 | Amano et al. |
| 2014/0278510 A1* | 9/2014 | McLean ................ G16H 20/13 705/2 |
| 2015/0190312 A1 | 7/2015 | Yuyama et al. |
| 2017/0135905 A1 | 5/2017 | Yuyama |
| 2018/0240541 A1* | 8/2018 | Ervin ........................ A61J 1/03 |

FOREIGN PATENT DOCUMENTS

| | | |
|---|---|---|
| JP | 2011-104077 A | 6/2011 |
| JP | 201764376 A | 4/2017 |
| JP | 2017137119 A | 8/2017 |
| TW | 201601982 A | 1/2016 |
| TW | 201613801 A | 4/2016 |
| WO | 2014/112221 A1 | 7/2014 |
| WO | WO-2014112221 A1 * | 7/2014 ................ A61J 3/00 |

OTHER PUBLICATIONS

Office Action in TW Application No. 108107061, dated Jan. 7, 2022. 12pp.
International Search Report in PCT/JP2019/008344, dated May 21, 2019. 2pp.
The Extended European Search Report in EP Application No. 19764030.3, dated Mar. 17, 2020. 10pp.
Office Action in JP Application No. 2019-536331, dated Sep. 27, 2022. 8pp.

* cited by examiner

FIG. 9
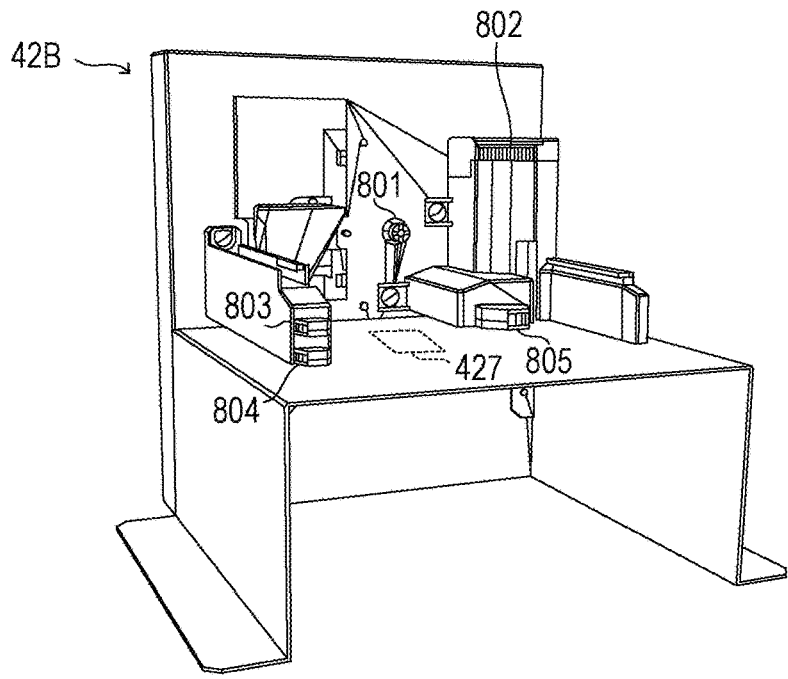
FIG. 10
FIG. 11
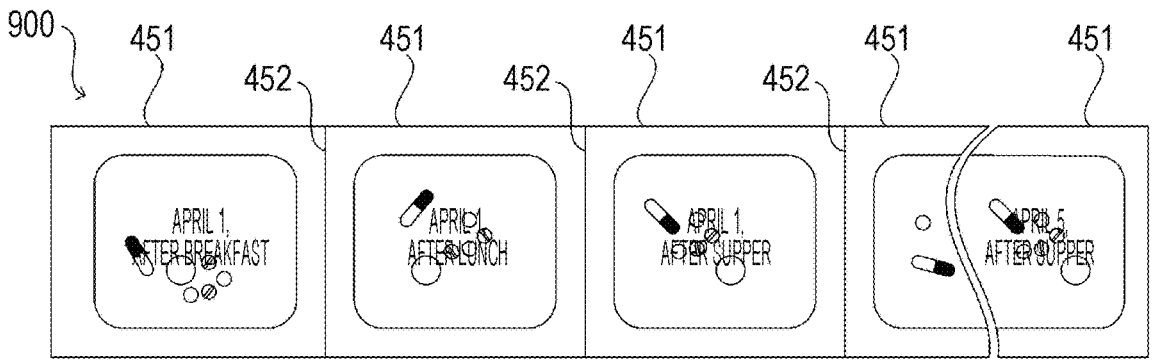

FIG. 13

| No. | Drug name |
|---|---|
| C1 | Drug M1 |
| C2 | Drug M2 |
| C3 | Drug M3 |
| C4 | Drug M4 |
| C5 | – |
| C6 | – |
| C7 | – |
| C8 | Drug M5 |

FIG. 14

| ID | PATIENT | Usage | Drug A | Drug B | Drug C | Drug D | Drug E |
|---|---|---|---|---|---|---|---|
| 001 | PATIENT P1 | 1day(m, n, e) | 2 | 2 | 2 | | |
| 002 | PATIENT P2 | 1day(m, n, e) | 2 | | | 2 | 1 |
| 003 | PATIENT P3 | 1day(m, n, e) | 2 | 2 | | 2 | |
| | | TOTAL | 18 | 12 | 6 | 12 | 3 |

FIG. 15

| No. | Drug name |
|---|---|
| C1 | Drug M1 |
| C2 | Drug M2 |
| C3 | Drug M3 |
| C4 | Drug M4 |
| C5 | Drug A (18 PILLS) |
| C6 | Drug B (12 PILLS) |
| C7 | Drug D (12 PILLS) |
| C8 | Drug M5 |

FIG. 16

| DTA CELL | Usage |
|---|---|
| 1A | PATIENT P1(m) Drug C : 2 |
| 2A | PATIENT P1(n) Drug C : 2 |
| 3A | PATIENT P1(e) Drug C : 2 |
| 4A | PATIENT P2(m) Drug E : 1 |
| 5A | PATIENT P2(n) Drug E : 1 |
| 6A | PATIENT P2(e) Drug E : 1 |
| 1B | |
| 2B | |
| 3B | |

FIG. 17

| ID | PATIENT | Usage | Drug A | Drug B | Drug C | Drug D | Drug E |
|---|---|---|---|---|---|---|---|
| 001 | PATIENT P1 | 1day(m, n, e) | 2 | 2 | 1 | | |
| 002 | PATIENT P2 | 1day(m, n) | 2 | | 1 | | 1 |
| | | 1day(e) | 2 | | | | 1 |
| 003 | PATIENT P3 | 1day(m, n) | 2 | 2 | | 2 | |
| | | 1day(e) | 2 | 2 | 1 | 2 | |
| | | TOTAL | 18 | 12 | 6 | 6 | 3 |

FIG. 18

| ID | PATIENT | Usage | Drug A | Drug B | Drug C | Drug D | Drug E |
|---|---|---|---|---|---|---|---|
| 001 | PATIENT P1 | 1day(m, n, e) | 2 | 2 | 1 | | |
| 002 | PATIENT P2 | 1day(m, n, e) | 2 | | 1 | | 1 |
| 003 | PATIENT P3 | 1day(m, n, e) | 2 | 2 | | 2 | |
| | | TOTAL | 18 | 12 | 6 | 6 | 3 |

FIG. 19

| DRUG ID | HEIGHT OF DISPENSING PATH | WIDTH OF DISPENSING PATH | DRIVING CONDITION | | | |
|---|---|---|---|---|---|---|
| | | | DISPENSING SPEED | FIRST SLOWDOWN | SECOND SLOWDOWN | REVERSE ROTATION OPERATION |
| M1 | h11 [mm] | w11 [mm] | v11 [PILLS/min] | sd11 [PILLS] | sd21 [PILLS] | YES |
| M2 | h12 [mm] | w12 [mm] | v12 [PILLS/min] | sd12 [PILLS] | sd22 [PILLS] | NO |
| M3 | h13 [mm] | w13 [mm] | v13 [PILLS/min] | sd13 [PILLS] | sd23 [PILLS] | NO |
| M4 | h14 [mm] | w14 [mm] | v14 [PILLS/min] | sd14 [PILLS] | sd24 [PILLS] | YES |
| ⋮ | ⋮ | ⋮ | ⋮ | ⋮ | ⋮ | ⋮ |

FIG. 20

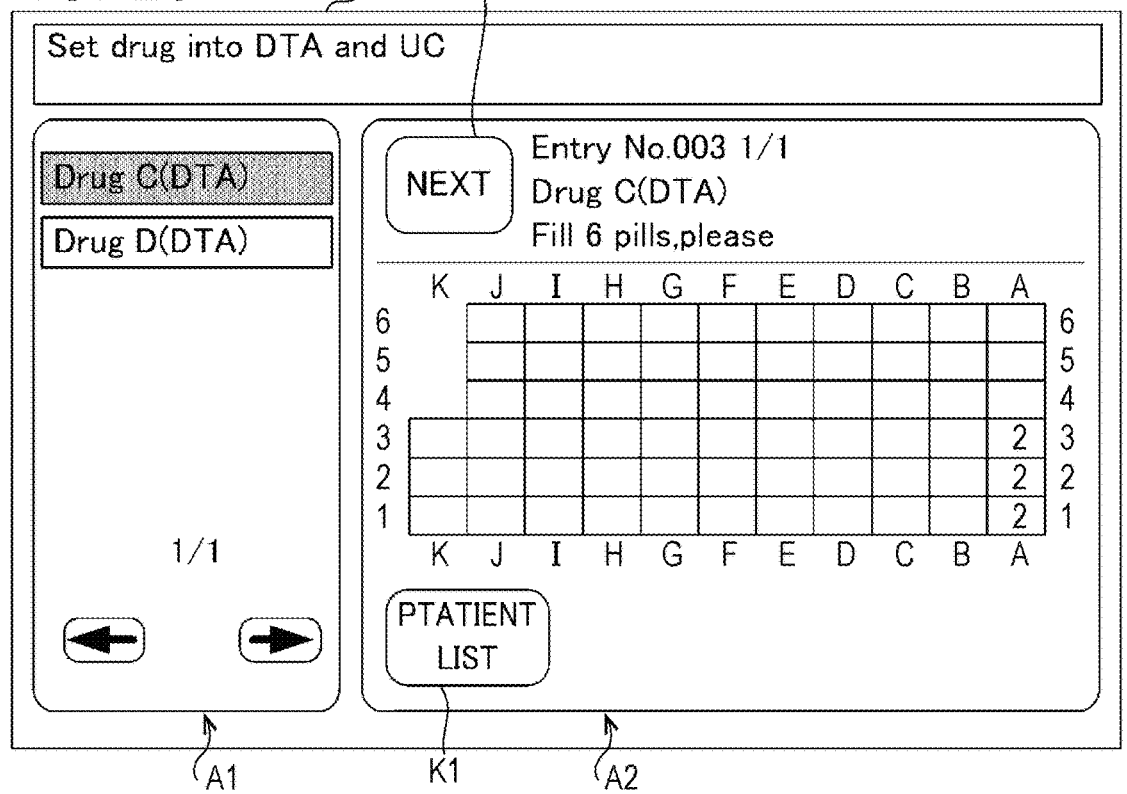

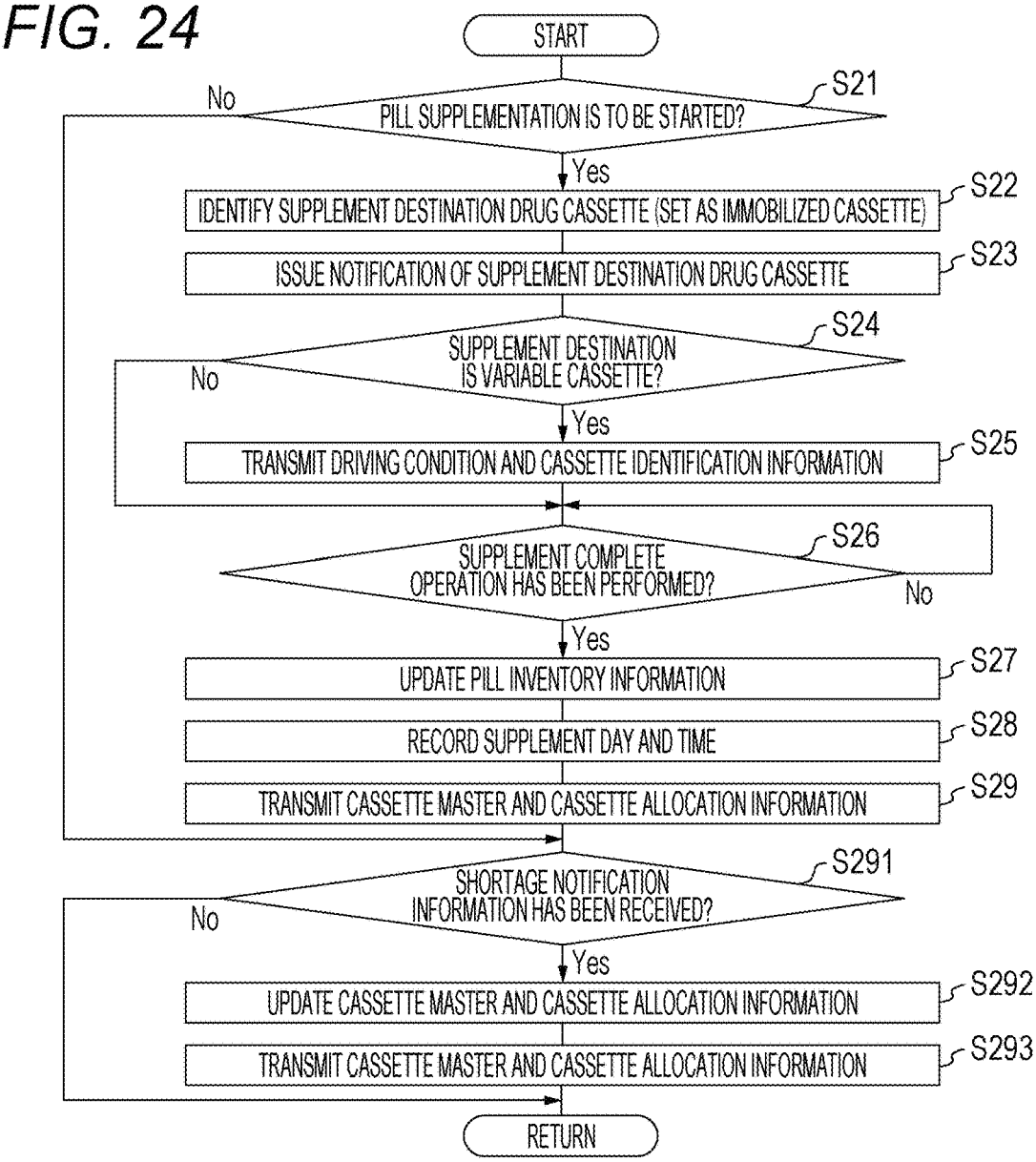

| No. | Drug name | Supplement day and time |
|---|---|---|
| C11 | Drug M1 | 20170102,11:23 |
| C12 | Drug M2 | 20170103,11:24 |
| C13 | Drug M3 | 20170104,11:25 |
| C14 | Drug M4 | 20170105,11:26 |
| C15 | Drug M5 | 20170106,11:27 |
| C16 | Drug M6 | 20170107,11:28 |
| C17 | Drug M7 | 20170108,11:29 |
| C18 | Drug M1 | 20170109,11:30 |
| ⋮ | ⋮ | ⋮ |

MEDICATION DISPENSING DEVICE, CONTROL METHOD, AND CONTROL PROGRAM

RELATED APPLICATIONS

The present application is National Phase of International Application Number PCT/JP2019/008344, filed Mar. 4, 2019, and claims priority based on Japanese Patent Application No. 2018-038587, filed Mar. 5, 2018.

TECHNICAL FIELD

The present invention relates to a drug dispensing device configured to dispense a drug contained in a drug cassette.

BACKGROUND ART

In general, there has been known a drug dispensing device, which includes a plurality of drug cassettes configured to contain various types of drugs, and which can dispense drugs from each of the drug cassettes based on prescription data, and package those drugs for each administration timing (see, for example, Patent Literature 1). This type of drug dispensing device includes a plurality of variable cassettes that can dispense any drug, and may dispense the drugs from the variable cassettes by appropriately allocating drug information on the drugs to be dispensed to each of the variable cassettes.

CITATION LIST

Patent Literature

[PTL 1] JP 2011-104077 A

SUMMARY OF INVENTION

Technical Problem

In a case in which prescription control processing is to be continuously executed for a plurality of pieces of prescription data, when drugs are dispensed by individually allocating the drugs to the variable cassettes for each packaging operation corresponding to the prescription data, efficiency of an operation of filling the drugs into the variable cassettes may deteriorate.

An object of the present invention is to provide a drug dispensing device, a control method, and a control program, which are capable of improving usage efficiency of variable cassettes at the time when prescription control processing is to be continuously executed for a plurality of pieces of prescription data.

Solution to Problem

A drug dispensing device according to one embodiment of the present invention includes: a variable cassette configured to dispense any type of drug; a mounting portion, to and from which the variable cassette is mountable and dismountable; an allocation processor configured to allocate, based on a plurality of pieces of prescription data, drug information on a drug to be dispensed included in the plurality of pieces of prescription data to the variable cassette or the mounting portion; and a drive controller configured to drive the variable cassette in accordance with a driving condition set in advance in association with the drug information allocated to the variable cassette or the mounting portion by the allocation processor, to thereby dispense from the variable cassette the drug corresponding to the plurality of pieces of prescription data.

A control method according to one embodiment of the present invention is a control method for a drug dispensing device, the drug dispensing device including a variable cassette configured to dispense any type of drug, and a mounting portion, to and from which the variable cassette is mountable and dismountable, the control method including: an allocation step of allocating, based on a plurality of pieces of prescription data, drug information on a drug to be dispensed included in the plurality of pieces of prescription data to the variable cassette or the mounting portion; and a driving step of driving the variable cassette in accordance with a driving condition set in advance in association with the drug information allocated to the variable cassette or the mounting portion in the allocation step, to thereby dispense from the variable cassette the drug corresponding to the plurality of pieces of prescription data.

A control program according to the present invention is a control program for causing a controller of a drug dispensing device including a variable cassette configured to dispense any type of drug, and a mounting portion, to and from which the variable cassette is mountable and dismountable, to execute: an allocation step of allocating, based on a plurality of pieces of prescription data, drug information on a drug to be dispensed included in the plurality of pieces of prescription data to the variable cassette or the mounting portion; and a driving step of driving the variable cassette in accordance with a driving condition set in advance in association with the drug information allocated to the variable cassette or the mounting portion in the allocation step, to thereby dispense from the variable cassette the drug corresponding to the plurality of pieces of prescription data.

Advantageous Effects of Invention

According to the present invention, it is possible to provide the drug dispensing device, the control method, and the control program, which are capable of improving the usage efficiency of variable cassettes at the time when prescription control processing is to be continuously executed on a plurality of pieces of prescription data.

BRIEF DESCRIPTION OF DRAWINGS

FIG. 9 is a view for illustrating an example of a mounting portion of the variable cassette of the drug dispensing device according to an embodiment of the present invention.

FIG. 10 is a view for illustrating an example of a drug palette of the drug dispensing device according to an embodiment of the present invention.

FIG. 11 is a view for illustrating an example of a packaging result in the drug dispensing device according to an embodiment of the present invention.

FIG. 13 is a table for showing an example of cassette allocation information to be used by the drug dispensing system in an embodiment of the present invention.

FIG. 14 is a table for showing an example of prescription data to be input to the drug dispensing device according to an embodiment of the present invention.

FIG. 15 is a table for showing an example of cassette allocation information to be used by the drug dispensing system in an embodiment of the present invention.

FIG. 16 is a table for showing an example of manual dispensing allocation information to be used by the drug dispensing system in an embodiment of the present invention.

FIG. 17 is a table for showing an example of prescription data to be input to the drug dispensing device according to an embodiment of the present invention.

FIG. 18 is a table for showing an example of prescription data to be input to the drug dispensing device according to an embodiment of the present invention.

FIG. 19 is a table for showing an example of drive correspondence information to be used by the drug dispensing system in an embodiment of the present invention.

FIG. 20 is a diagram for illustrating an example of a display screen displayed by the drug dispensing system in an embodiment of the present invention.

FIG. 24 is a flowchart for illustrating an example of pill supplement processing to be executed by the drug dispensing system in an embodiment of the present invention.

FIG. 25A is a table for showing an example of cassette allocation information to be used by the drug dispensing system in an embodiment of the present invention.

DESCRIPTION OF EMBODIMENTS

An embodiment of the present invention is now described with reference to the accompanying drawings for understanding of the present invention. The following embodiment is an example in which the present invention is embodied, and is not intended to limit the technical scope of the present invention. Further, the configurations and processing functions described in the following embodiment may be optionally selected and freely combined.

[Drug Dispensing System 1]

Figure 1:
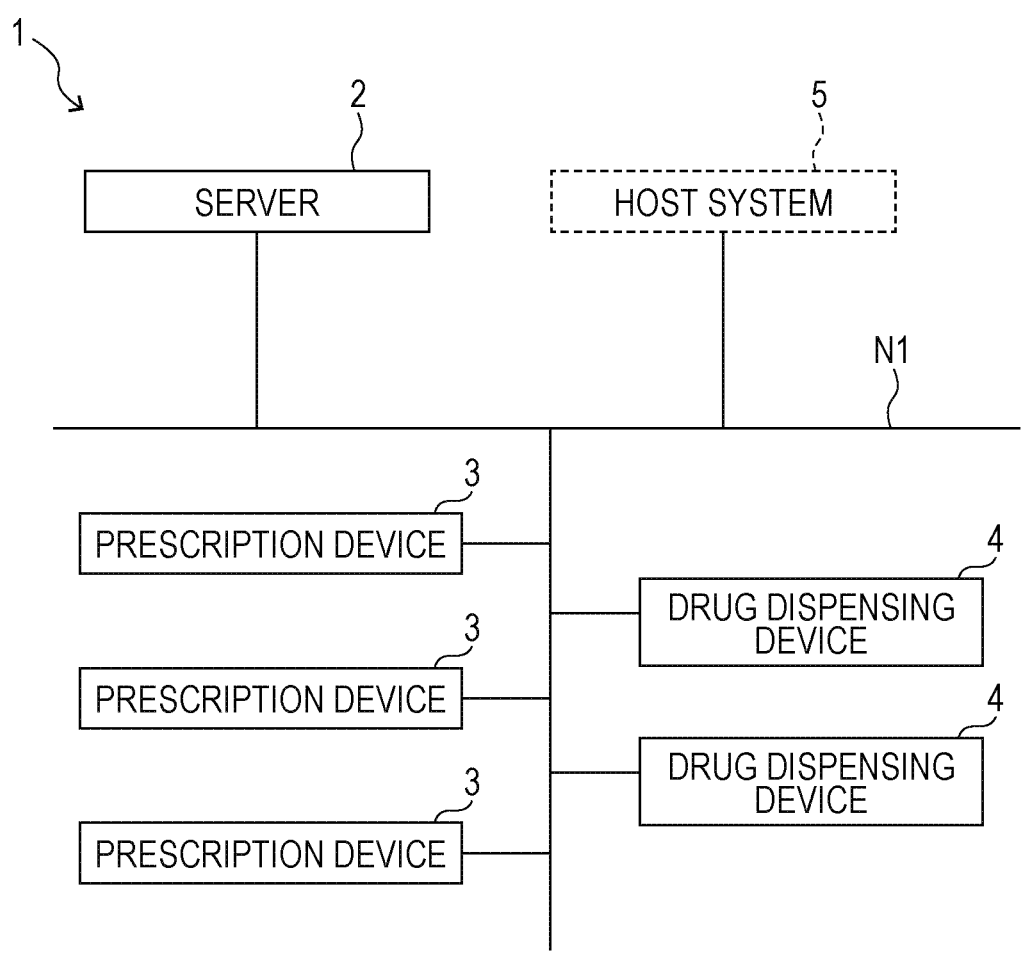
FIG. 1 is a diagram for illustrating a configuration of a drug dispensing system in an embodiment of the present invention.

As illustrated in FIG. 1, a drug dispensing system 1 in an embodiment of the present invention includes a server 2, one or a plurality of prescription devices 3, and one or a plurality of drug dispensing devices 4. The server 2, the prescription devices 3, and the drug dispensing devices 4 are connected wirelessly or by a cable in a communicable manner via a communication network N1, such as a LAN or the Internet.

A host system 5, such as an electronic medical record system or a prescription input terminal for inputting prescription data to the server 2, is connected to the server 2 via the communication network N1. The server 2 is configured to appropriately distribute and transmit prescription data input from the host system 5, prescription data read by the code reader 27, and the like to the prescription devices 3 and the drug dispensing devices 4. As a result, processing for dispensing drug based on the prescription data is executed by the prescription devices 3 and the drug dispensing devices 4. Specifically, the drug dispensing device 4 is a pill dispensing device that can dispense and package at least a pill.

The prescription data includes, for example, a patient name, a patient ID, whether a patient is hospitalized or an outpatient, a ward, a doctor in charge, a drug ID of a prescription drug, a drug name, a dose/use, and the like. The prescription data in this embodiment includes prescription drug data for one day or a plurality of days. The prescription devices 3 and the drug dispensing devices 4 may be configured to access the server 2 to actively acquire the prescription data. The server 2, the prescription devices 3, and the drug dispensing devices 4 may also read, from a two-dimensional code or the like written on a prescription being a paper medium, the prescription data corresponding to the prescription, or may receive any input of the prescription data by a user operation.

The prescription device 3 is a device to be used when a drug is prepared based on prescription data. For example, the prescription device 3 includes a powdered drug packaging device, a liquid medicine dispensing device, and a sheet dispensing device. The powdered drug dispensing device includes a plurality of powdered drug cassettes containing a plurality of types of powdered drugs, and can automatically package, in accordance with the prescription data, a predetermined amount of the powdered drugs contained in the powdered drug cassettes. The liquid medicine dispensing device includes a plurality of medicine bottles containing a plurality of types of liquid medicines, and dispenses a required amount of liquid medicine from the medicine bottles in accordance with the prescription data. The sheet dispensing device is configured to dispense, in accordance with the prescription data, a PTP sheet or a heat-sealed sheet in which a drug has been packaged in advance from a plurality of sheet cassettes containing PTP sheets or heat-sealed sheets.

[Drug Dispensing Device 4]

The drug dispensing device 4 is now described with reference to FIG. 2 to FIG. 11.

Figure 2:
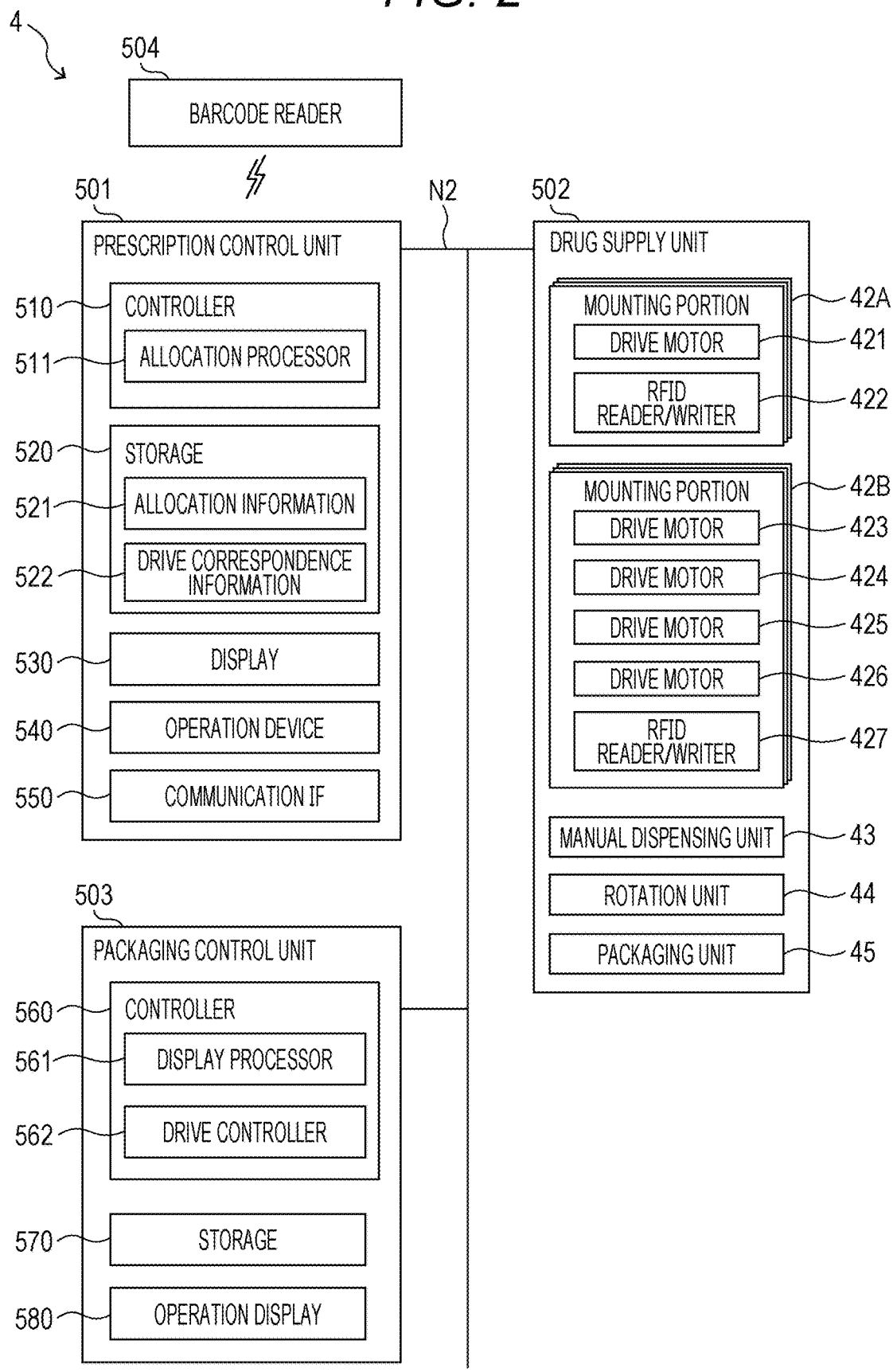
FIG. 2 is a diagram for illustrating a configuration of a drug dispensing device according to an embodiment of the present invention.
Figure 3:
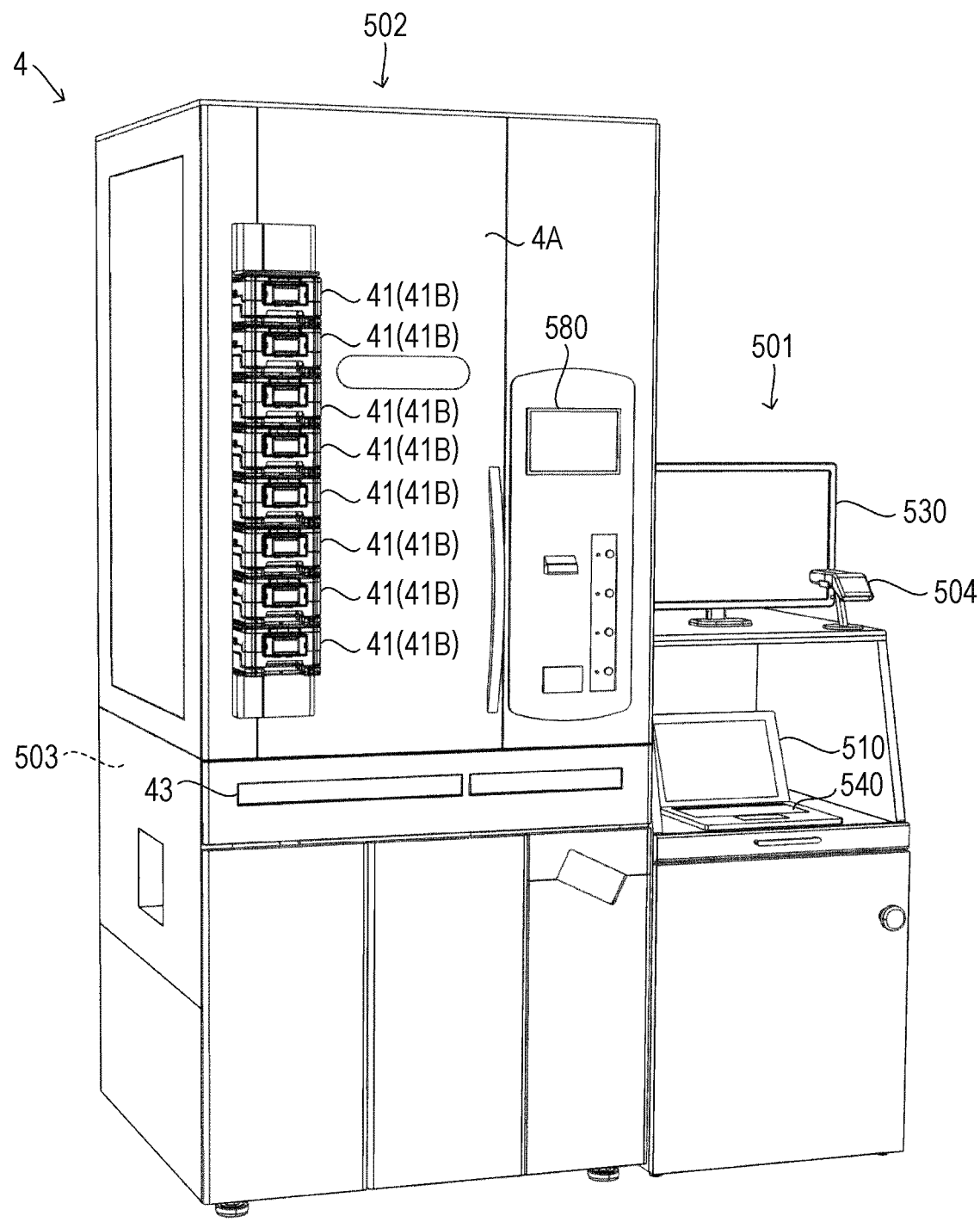
FIG. 3 is an external view of the drug dispensing device according to an embodiment of the present invention.

As illustrated in FIG. 2 and FIG. 3, the drug dispensing device 4 includes a prescription control unit 501, a drug supply unit 502, a packaging control unit 503, a barcode reader 504, and the like. The prescription control unit 501, the drug supply unit 502, and the packaging control unit 503 are connected by an internal bus N2. The prescription control unit 501 and the barcode reader 504 can perform wireless communication in accordance with a communication standard such as wireless LAN or short-range wireless communication.

In the drug dispensing device 4, a packaging operation is executed in which a drug is dispensed from the drug supply unit 502 based on the prescription data and the drug is packaged into a drug package by the packaging unit 45 in units of package, for example, a time of administration. In the drug dispensing device 4 according to this embodiment, the prescription control unit 501 and the packaging control unit 503 cooperate to execute various types of processes for implementing the packaging operation, but the various types of processes may be executed by a single controller.

[Prescription Control Unit 501]

The prescription control unit 501 is a computer configured to control the drug dispensing devices 4 in an integrated manner. As illustrated in FIG. 2 and FIG. 3, the prescription control unit 501 includes a controller 510, a storage 520, a display 530, an operation device 540, a communication IF 550, and the like.

The controller 510 is control means including a CPU, a RAM, a ROM, an EEPROM (trademark), and the like. The controller 510 is configured to execute various types of processing by the CPU in accordance with various types of programs stored in advance in storage means such as the ROM, the EEPROM, or the storage 520. The CPU is a processor configured to execute various types of processing. The RAM and the EEPROM are used as a temporary storage memory (working area) for various types of processing to be executed by the CPU. The controller 510 may be an electric circuit including an ASIC or a DSP.

The storage 520 is nonvolatile storage means for storing various types of data, such as a hard disk drive (HDD) or a solid state drive (SSD). Specifically, the storage 520 stores in advance a control program for causing a computer, for example, the controller 510, to execute prescription control processing described later (see left side of FIG. 12).

The control program is recorded on a computer-readable recording medium such as a CD, a DVD, or a semiconductor memory. The control program is read from the recording medium by a reading device, for example, a disk drive (not shown), and installed in the storage 520. The present invention can be understood as an invention of the computer-readable recording medium having the above-mentioned control program recorded thereon.

Specifically, the controller 510 includes an allocation processor 511. The controller 510 functions as the allocation processor 511 by executing various types of processing in accordance with the control program. The allocation processor 511 may be configured as an electric circuit.

The allocation processor 511 can allocate, based on a plurality of pieces of prescription data, drug information on the drugs to be dispensed included in the plurality of pieces of prescription data to variable cassettes 41B or mounting portions 42B, which are described later. The drug information is information that can be used to identify the type of the drug. More specifically, the allocation processor 511 allocates, in units of the plurality of pieces of prescription data, drug information on the drug to be dispensed included in the plurality of pieces of prescription data in accordance with an allocation rule set in advance to the variable cassette 41B or the mounting portion 42B. The allocation rule is described later.

Figures 25B, 26:
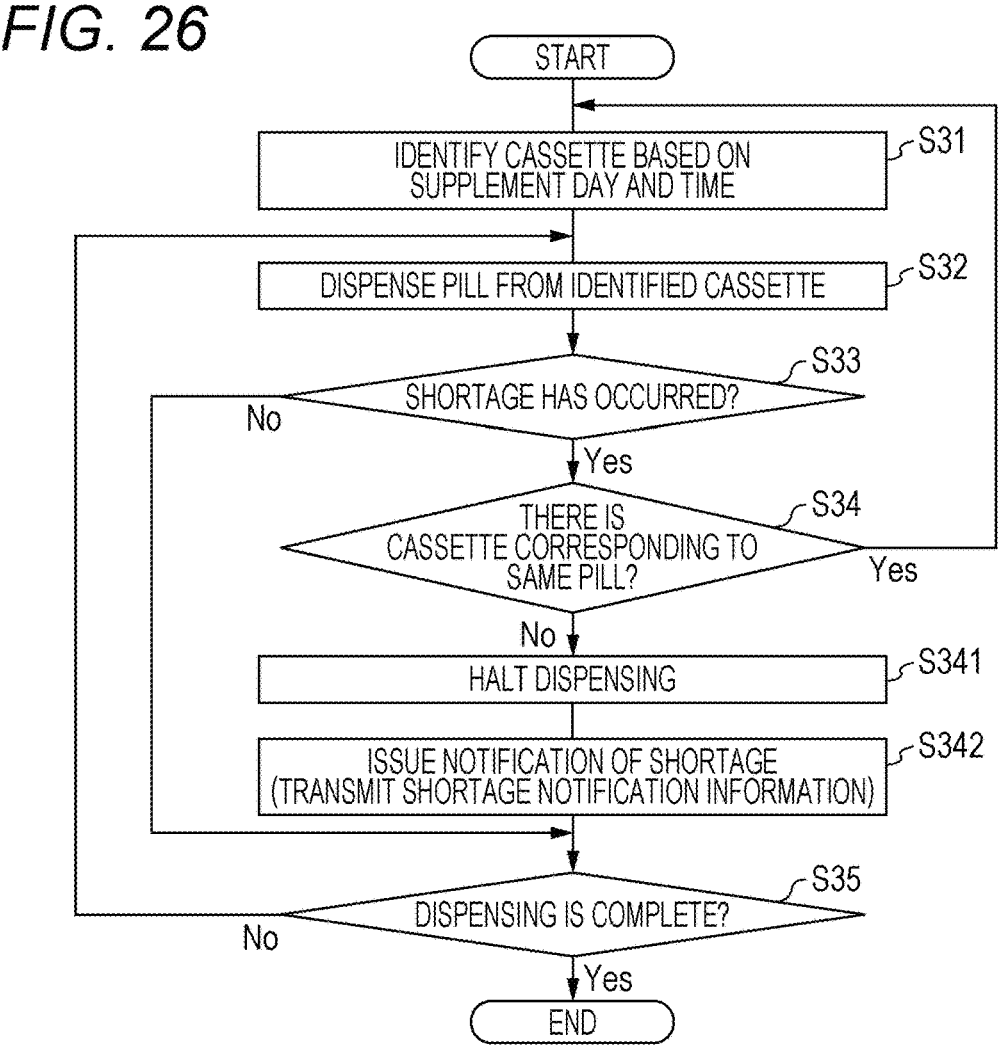
FIG. 25B is a table for showing an example of a cassette master to be used by the drug dispensing system in an embodiment of the present invention.
FIG. 26 is a flowchart for illustrating an example of pill dispensing processing to be executed by the drug dispensing system in an embodiment of the present invention.

The storage 520 also stores various types of databases, such as a patient master, a pharmacy master, a medicine master, and a cassette master 524 (e.g., see FIG. 25B). The controller 510 can update the various types of databases stored in the storage 520 based on, for example, data read from a recording medium such as a CD, a DVD, or a semiconductor memory by a reading device, for example, a disk drive (not shown). The controller 510 can change the content of the various types of databases in response to a user operation on the operation device 540.

The patient master includes information on patients, such as a patient ID, a name, a gender, an age, a medical history, a prescription drug history, family information, a clinical department, a ward, and a room. The pharmacy master includes information on pharmacies, such as a pharmacy name, a pharmacist name, and a pharmacist ID.

The medicine master includes information on each medicine, such as a drug ID, a drug code, a drug name, a JAN code (or RSS code), a medicine bottle code, a classification (dosage form: powdered drug, pill, liquid medicine, topical medicine, and the like), a drug size (height and width), a specific gravity, a drug type (ordinary drug, poison, narcotic, powerful drug, antipsychotic, therapeutic drug, and the like), a formulation variation, a pharmaceutical excipient, and a precaution.

The cassette master 524 is master information indicating a correspondence relationship between cassette identification information that can be used to identify each fixed cassette 41A, which is described later, included in the drug supply unit 502 and drug information that can be used to identify drugs dispensable from each fixed cassette 41A. As a result, the drug dispensing device 4 can determine the type of drug that is dispensable from each of the fixed cassettes 41A based on the cassette master 524. The cassette master 524 is registered by the controller 510 in response to a user operation of the operation device 540 in the initial setting of the drug dispensing device 4, for example, and can be updated as appropriate in response to the user operation of the operation device 540. The information shown in the cassette master 524 may be stored in the storage 520 as one item of the medicine master. For example, for each piece of drug information included in the medicine master, a presence/absence of the corresponding fixed cassette 41A and the cassette identification information on the fixed cassette 41A allocated to the piece of drug information may be stored.

The display 530 is display means, for example, a liquid crystal monitor, for displaying various types of information and operation screens in accordance with a control instruction from the controller 510. For example, the display 530 displays various types of information such as a prescription data input screen and a prescription data selection screen.

The operation device 540 is operation means for receiving a user operation, such as an operation button, a keyboard, a mouse, or a touch panel. The operation device 540 inputs an operation signal corresponding to the user operation to the controller 510. The operation device 540 is configured to receive various types of operations, such as an operation of inputting prescription data on the input screen displayed on the display 530, an operation of selecting prescription data on the selection screen, and an operation of issuing prescription data, which requests the start of packaging the prescription data.

The communication IF 550 is a communication interface for connecting the drug dispensing device 4 to the communication network N1, for example, a LAN. The communication IF 550 is configured to execute data communication to and from the server 2 connected via the communication network N1. The communication IF 550 also includes a wireless communication interface, for example, a wireless communication module configured to perform wireless data communication to and from various types of wireless communication devices, for example, the barcode reader 504.

Under the controller 510, the communication IF 550 acquires prescription data from the server 2, and stores the prescription data in the storage 520. For example, the communication IF 550 monitors whether or not prescription data is newly stored in a predetermined storage area of the storage 22 included in the server 2. When prescription data is newly stored in the predetermined storage area, the communication IF 550 reads the prescription data from the predetermined storage area. It is to be understood that the communication IF 550 may also acquire the prescription data by receiving the prescription data transmitted in an appropriate manner from the server 2.

[Drug Supply Unit 502]

Figure 4:
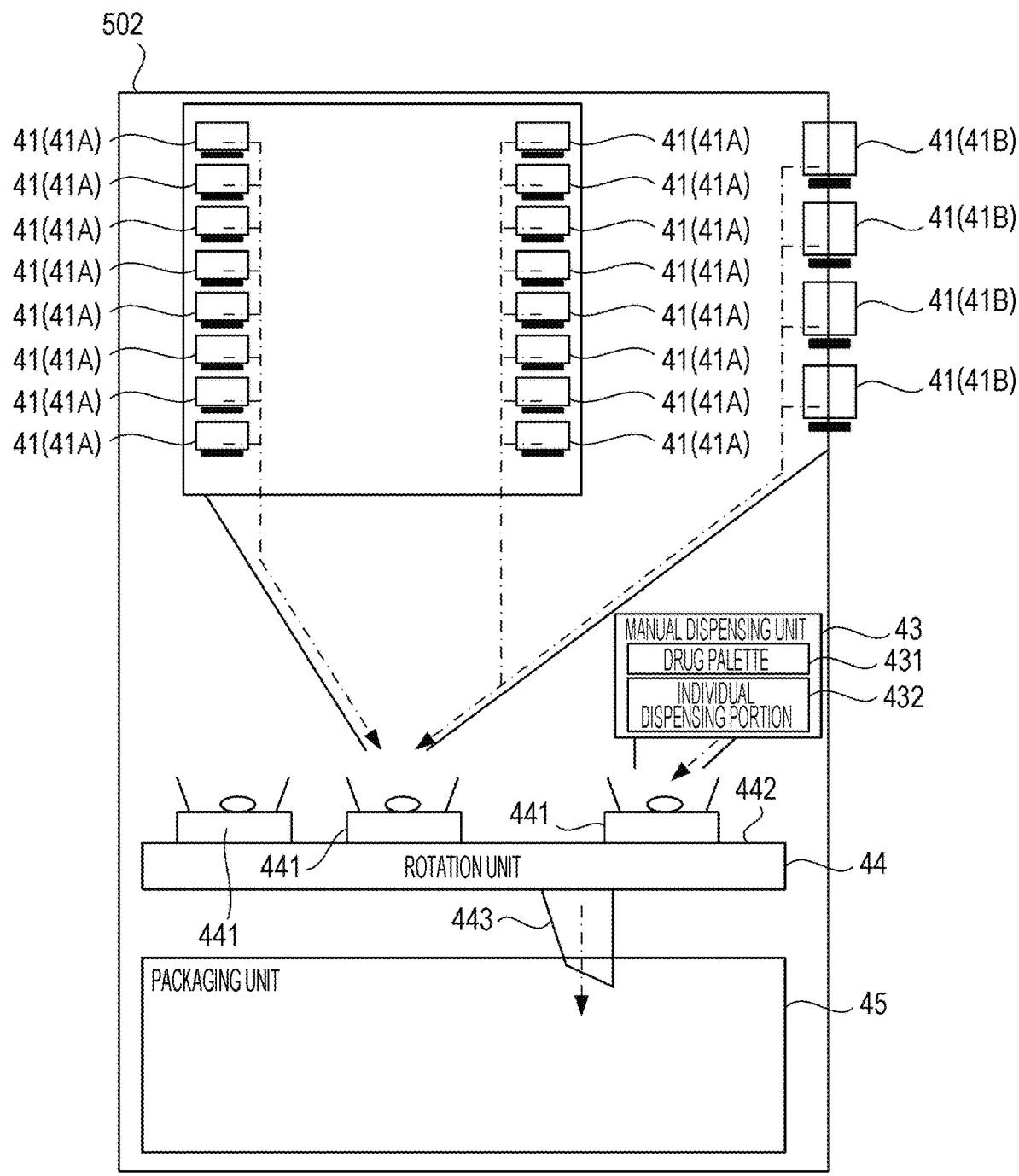
FIG. 4 is a schematic diagram for illustrating an internal configuration of the drug dispensing device according to an embodiment of the present invention.

As illustrated in FIG. 2 to FIG. 4, the drug supply unit 502 includes a plurality of drug cassettes 41, a plurality of mounting portions 42, a manual dispensing unit 43, a rotation unit 44, a packaging unit 45, and the like. A front door 4A of the drug supply unit 502 can be opened and closed.

The plurality of drug cassettes 41 include a plurality of fixed cassettes 41A, which can dispense a predetermined specific type of drug for each pill (unit amount), and a plurality of variable cassettes 41B, which can dispense any type of drug for each pill (unit amount) by changing a driving condition. The drug that can be dispensed by the fixed cassette 41A and the variable cassette 41B may be various types of forms of pills, for example, a pill having a disc shape, a spherical shape, or a capsule shape. As another embodiment, the drug supply unit 502 does not include the fixed cassettes 41A, and only includes a plurality of variable cassettes 41B.

The plurality of mounting portions 42 include a plurality of mounting portions 42A, to/from which the fixed cassettes 41A can be mounted and dismounted, and a plurality of mounting portions 42B, to which the variable cassettes 41B are mountable. The mounting portions 42A are arranged inside the drug dispensing device 4, and the user can mount and dismount a fixed cassette 41A to and from a mounting portion 42A by opening the front door 4A of the drug dispensing device 4. The mounting portions 42B are arranged on the front surface of the drug dispensing device 4, and the user can mount and dismount a variable cassette 41B to and from a mounting portion 42B without opening the front door 4A of the drug dispensing device 4.

Each mounting portion 42A includes a drive motor 421 and an RFID reader/writer 422. The drive motor 421 is controlled by the packaging control unit 500, and is configured to supply a drive force to a drive mechanism of a fixed cassette 41A to cause a drug to be dispensed from the fixed cassette 41A. The RFID reader/writer 422 can, by using radio frequency identification (RFID) wireless communication technology, read information from an RFID tag (not shown) arranged on the fixed cassette 41A or write information to the RFID tag. For example, the RFID reader/writer 422 is used in order to read identification information on the fixed cassette 41A from the RFID of the fixed cassette 41A.

Each mounting portion 42B includes drive motors 423 to 426 and an RFID reader/writer 427. The drive motors 423 to 426 are controlled by the packaging control unit 500, and are configured to supply a drive force to a drive mechanism of a variable cassette 41B to cause a drug to be dispensed from the variable cassette 41B. The RFID reader/writer 422 can, by using radio frequency identification (RFID) wireless communication technology, read information from an RFID 427A (see FIG. 8) arranged on the variable cassette 41B or write information to the RFID tag 427A.

The RFID tag 427A is a non-volatile recording medium in which cassette identification information for identifying each of the variable cassettes 41B, drug information on the drug allocated to the variable cassette 41B in prescription control processing (see the left side of FIG. 12), and the like described later are recorded. The drug information is information that can be used to identify the type of drug, and is, for example, a drug name, a drug ID, a drug code, a JAN code, an RSS code, or a QR code (trademark). The JAN code and the RSS code are numerical or character information expressed by a one-dimensional code (barcode, GS1 code), and the QR code is numerical or character information expressed by a two-dimensional code.

[Fixed Cassette 41A]

Figure 5:
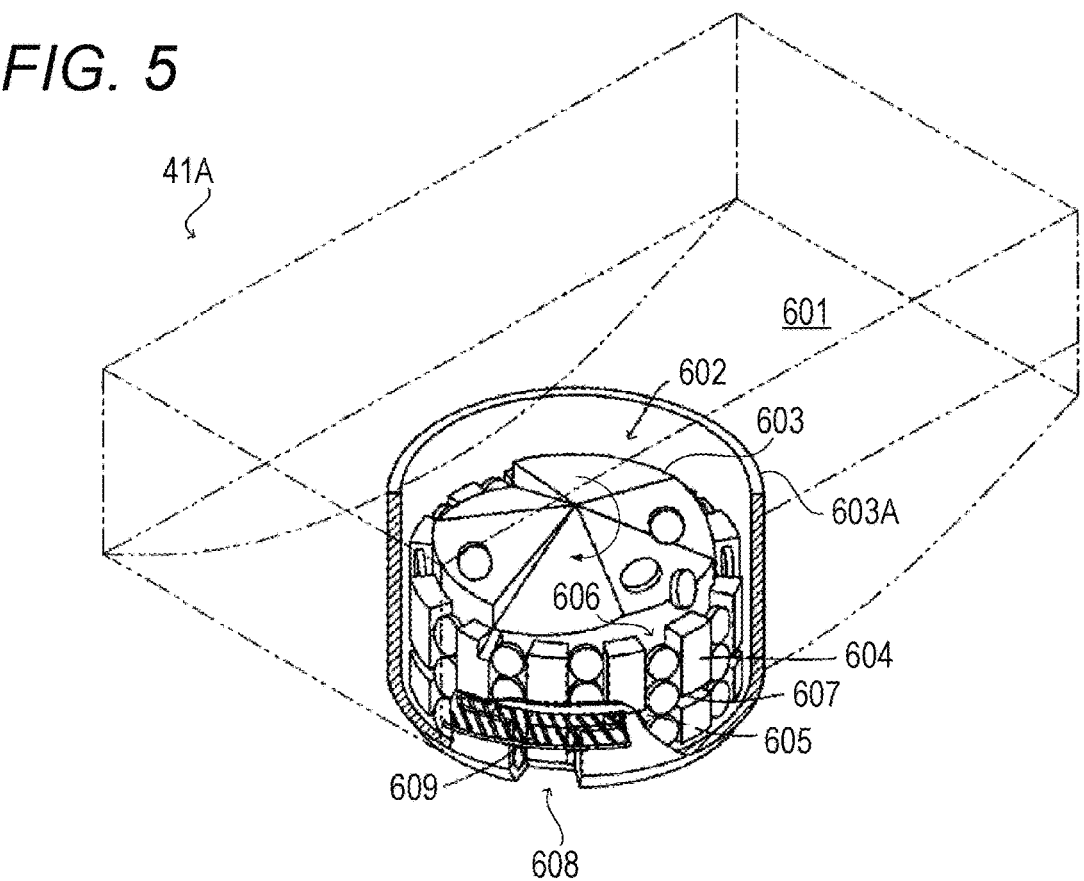
FIG. 5 is a view for illustrating an example of a fixed cassette of the drug dispensing device according to an embodiment of the present invention.

An example of the fixed cassette 41A is now described with reference to FIG. 5. The structure of the fixed cassette 41A described here is merely an example, and another structure may be employed as long as the structure has similar functions. In FIG. 5, a cover member for covering an upper portion of the fixed cassette 41A is omitted.

The type of drug to be contained in each of the fixed cassettes 41A is determined in advance. Therefore, for example, drug information on the drug to be contained in each fixed cassette 41A is written in advance on the front surface of fixed cassette 41A.

As illustrated in FIG. 5, each fixed cassette 41A includes a drug containing portion 601 configured to contain a large quantity of drugs, and a drug discharging portion 602 configured to individually discharge the drugs contained in the drug containing portion 601. The drug discharging portion 602 is provided in a recessed portion formed at a substantially central portion of the drug containing portion 601, and the drugs in the drug containing portion 601 are sequentially lowered toward the drug discharging portion 602.

The drug discharging portion 602 includes a rotor 603 rotatably supported by a housing of the fixed cassette 41A, and an inner wall 603A covering an outer periphery of the rotor 603. The rotor 603 is connected to the drive motor 421 of the mounting portion 42A via a drive transmission system (not shown), for example, various types of gears, when the fixed cassette 41A is mounted on the mounting portion 42A. Ribs 604 and ribs 605 are formed on the outer peripheral surface of the rotor 603 at arrangement intervals determined in advance. As a result, gaps 606 surrounded by the ribs 604, the ribs 605, and the inner wall 603A are intermittently formed on the outer periphery of the rotor 603. The width of the gaps 606 is determined in accordance with the type of drug determined in advance as the drug to be contained in the fixed cassette 41A, and corresponds to the width of one pill of the drug.

Gaps 607 are formed between the ribs 604 and the ribs 605 over the entire outer peripheral surface of the rotor 603. The height of the upper edge of each rib 604 and rib 605 is determined in accordance with the type of drug determined in advance as the drug to be contained in the fixed cassette 41A. Specifically, the height of the upper edge of the ribs 604 illustrated in FIG. 5 corresponds to the height of three pills of the drug, and three pills of the drug are inserted into each gap 606 of the rotor 603. The height of the upper edge of the ribs 605 corresponds to the height of one pill of the drug.

Meanwhile, a discharge port 608 for discharging the drug from the rotor 603 is formed on the inner wall 603A, and a partition plate 609 inserted into the gap 607 is arranged in the discharge port 608. As a result, at the discharge port 608, of the three pills of the drug inserted in the gap 606, the upper two pills are prevented from dropping down by the partition plate 609, and only the lower one pill is discharged. Therefore, in the fixed cassette 41A, the drug contained in the drug containing portion 601 is dispensed in units of one pill when the rotor 603 is driven by the drive motor 421.

[Variable Cassette 41B]

Next, an example of the variable cassette 41B is described with reference to FIG. 6 to FIG. 9. The variable cassette 41B is also disclosed in, for example, WO 2014/112221 A1. The structure of the variable cassette 41B described here is merely an example, and another structure may be employed as long as any type of drug can be dispensed one pill at a time. For example, in JP 2010-535683 A and JP 2010-115493 A, there are disclosed other examples of the variable cassette 41B.

Figure 6:
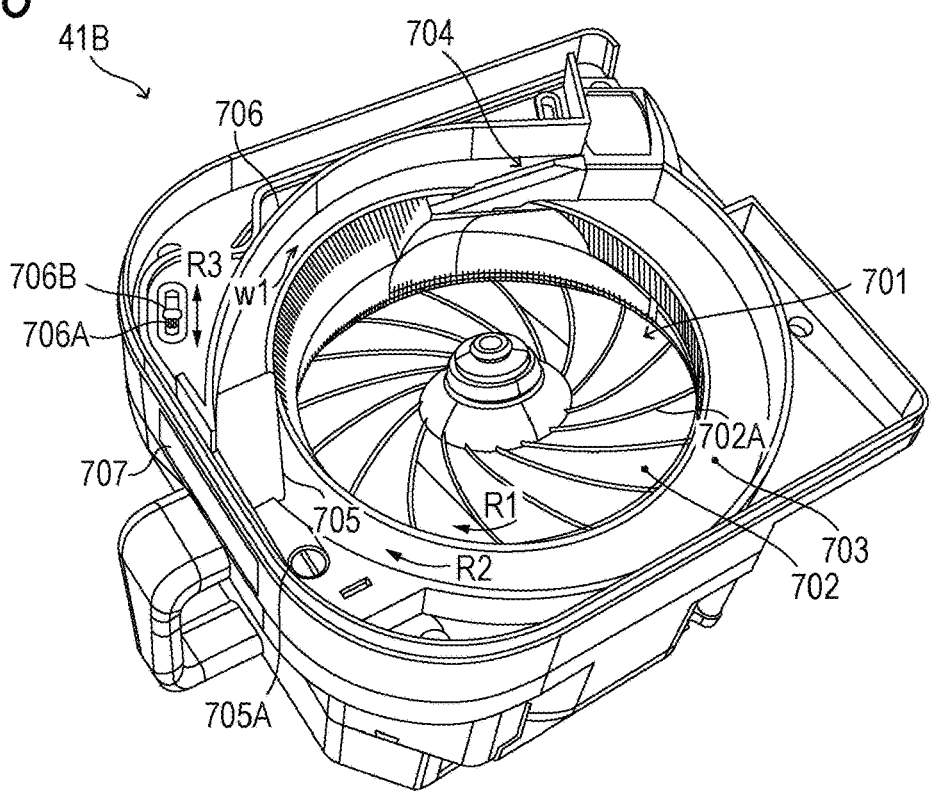
FIG. 6 is a view for illustrating an example of a variable cassette of the drug dispensing device according to an embodiment of the present invention.
Figure 7:
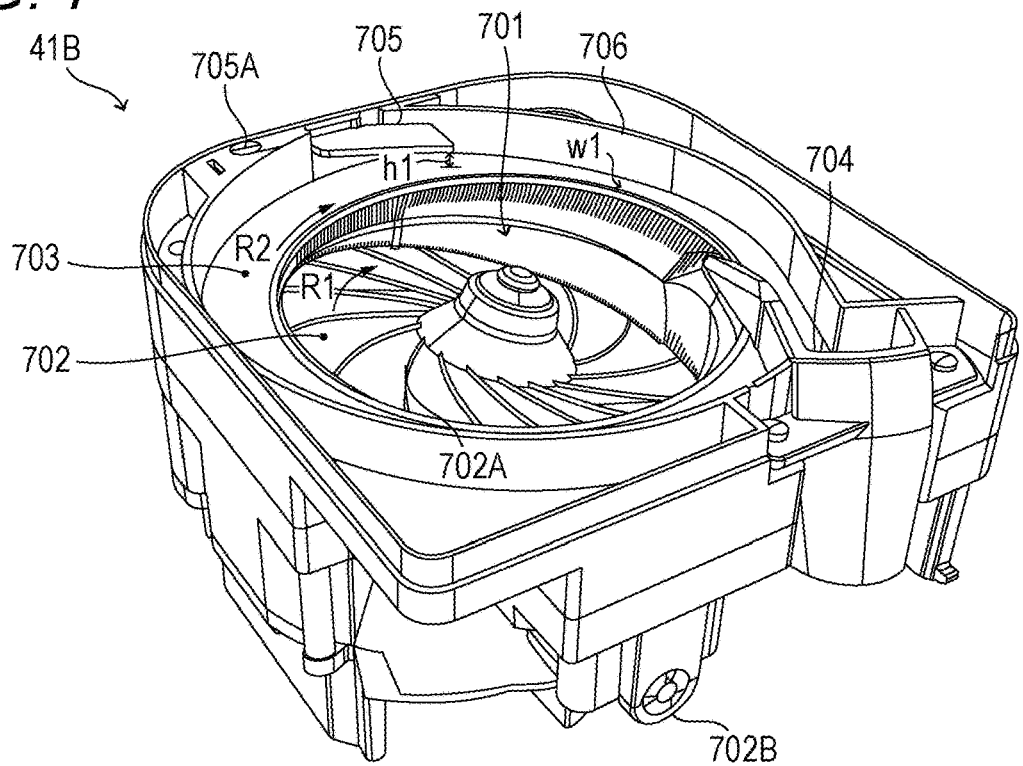
FIG. 7 is a view for illustrating an example of the variable cassette of the drug dispensing device according to an embodiment of the present invention.
Figure 8:
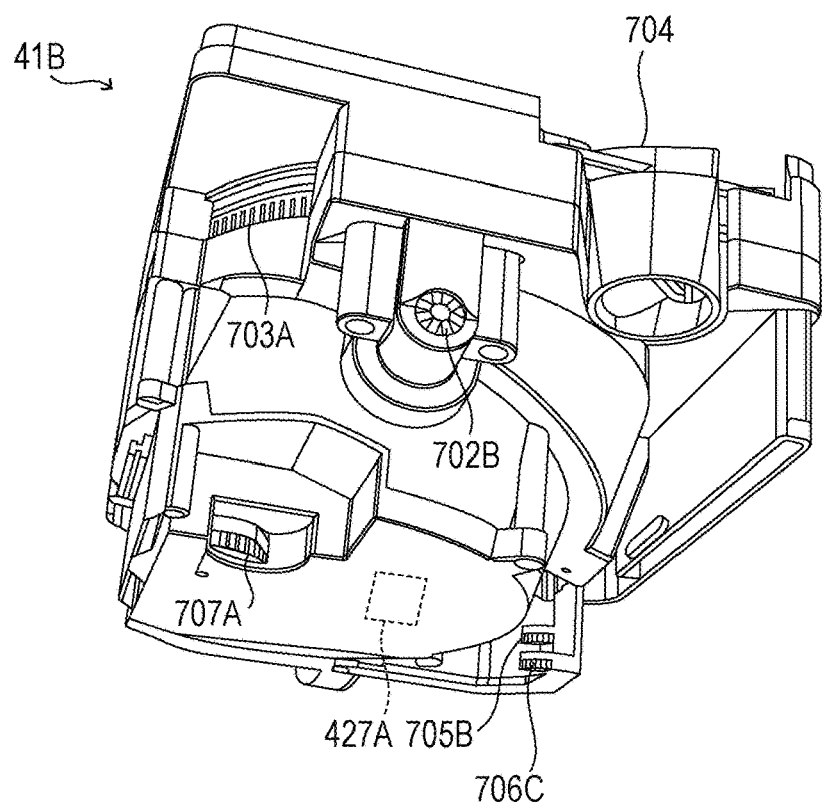
FIG. 8 is a view for illustrating an example of the variable cassette of the drug dispensing device according to an embodiment of the present invention.

As illustrated in FIG. 6 to FIG. 8, the variable cassette 41B includes a drug containing portion 701 configured to contain a large quantity of drugs, and a first rotating body 702 and a second rotating body 703 configured to dispense a drug from the drug containing portion 701. In FIG. 6 to FIG. 8, a cover member for covering an upper portion of the variable cassette 41B is omitted. The variable cassette 41B is only required to be able to dispense a drug for each unit amount determined in advance, and for example, the variable cassette 41B may be configured to dispense a plurality of pills in place of just one pill.

The first rotating body 702 is a disc-shaped member forming the bottom surface of the drug containing portion 701. A rotation axis of the first rotating body 702 is inclined by a predetermined angle determined in advance with respect to the vertical direction, and the upper surface of the first rotating body 702 is inclined by the predetermined angle with respect to the horizontal plane. Radial ribs 702A are formed on the upper surface of the first rotating body 702 at predetermined intervals. The first rotating body 702 is rotatably supported by the housing of the variable cassette 41B, and is connected to a driving gear 702B illustrated in FIG. 7 and FIG. 8.

A second rotating body 703 is a hollow annular member disposed around the first rotating body 702 in plan view, and is an example of a conveying member configured to convey the drug of the drug containing portion 701 to a dispensing port 704 and dispense the drug from the dispensing port 704. An upper edge of the first rotating body 702 is positioned on the same horizontal plane as that of the second rotating body 703. The second rotating body 703 is rotatably supported by the housing of the variable cassette 41B, and a driving gear 703A illustrated in FIG. 8 is formed on an outer peripheral surface.

Meanwhile, as illustrated in FIG. 9, a driving gear 801 connected to a driving gear 702B of the first rotating body 702 and a driving gear 802 connected to a driving gear 703A of the second rotating body 703 are arranged on the mounting portion 42B when the variable cassette 41B is mounted. The driving gear 801 is connected to a drive motor 423 of the mounting portion 42B, and the driving gear 802 is connected to a drive motor 424 of the mounting portion 42B.

Further, as illustrated in FIG. 6 and FIG. 7, the variable cassette 41B includes a height regulating member 705 and a width regulating member 706 arranged on a dispensing path of the drug to be conveyed to the dispensing port 704 by the second rotating body 703.

The height regulating member 705 is configured to regulate the size in the height direction of the drugs that can be conveyed to the dispensing port 704 by the second rotating body 703, and the width regulating member 706 is configured to regulate the size in the width direction of the drugs that can be conveyed to the dispensing port 704 by the second rotating body 703.

The variable cassette 41B includes a height adjustment portion 705A for changing a height h1 to be regulated by the height regulating member 705, and a width adjustment portion 706A for changing a width w1 to be regulated by the width regulating member 706. A pinion gear engaged with a rack (gear) formed on an inner peripheral surface of an elongated hole 706B formed in the width regulating member 706 is formed on the outer peripheral surface of the width adjusting portion 706A.

The height adjustment portion 705A is rotatably supported by the housing of the variable cassette 41B, and is connected to a driving gear 705B illustrated in FIG. 8. The height adjustment portion 705A is rotationally driven to move the position of a lower edge of the height regulating member 705 up and down to change the height h1 to be regulated by the height regulating member 705.

The width adjustment portion 706A is rotatably supported by the housing of the variable cassette 41B, and is connected to a driving gear 706C illustrated in FIG. 8. The width adjustment portion 706A is rotationally driven to change a protrusion amount of the width regulating member 706 toward the drug containing portion 701 side, and change the width w1 to be regulated by the width regulating member 706. Specifically, the protrusion amount of the width regulating member 706 toward the drug containing portion 701 side is changed by rotating the width adjustment portion 706A such that the width adjustment portion 706A and the elongated hole 706B are each relatively moved in the direction of an arrow R3 (see FIG. 6).

Meanwhile, as illustrated in FIG. 9, a driving gear 803 connected to the driving gear 705B and a driving gear 804 connected to the driving gear 706C are arranged on the mounting portion 42B when the variable cassette 41B is mounted. The driving gear 803 is connected to a drive motor 425 of the mounting portion 42B, and the driving gear 804 is connected to a drive motor 426 of the mounting portion 42B.

As illustrated in FIG. 8 and FIG. 9, the variable cassette 41B and the mounting portion 42B include a driving gear 707A and a driving gear 805, which are connected when the variable cassette 41B is mounted to the mounting portion 42B. The driving gear 707A is connected to a raising and lowering mechanism (not shown) configured to move the first rotating body 702 up and down, and the driving gear 805 is connected to a drive motor (not shown). As a result, when the drive motor is driven, a drive force is transmitted from the driving gear 805 to the driving gear 707A, and the first rotating body 702 can be moved up and down by the raising and lowering mechanism.

In the variable cassette 41B, when the first rotating body 702 is rotated in a rotation direction R1 (see FIG. 6 and FIG. 7), the drug of the drug containing portion 701 is discharged from the first rotating body 702 to the second rotating body 703. In the variable cassette 41B, when the second rotating body 703 is rotated in a rotation direction R2 (see FIG. 6 and FIG. 7), the drug on the second rotating body 703 is conveyed toward the dispensing port 704.

However, of the drugs conveyed by the second rotating body 703, the drugs stacked in the height direction come into contact with the height regulating member 705, and are returned to the drug containing portion 701. Further, of the drugs conveyed by the second rotating body 703, the drugs conveyed side by side in the width direction come into contact with the width regulating member 706, and are returned to the drug containing portion 701.

As a result, in the variable cassette 41B, drugs having a size corresponding to the height h1 to be regulated by the height regulating member 705 and the width w1 to be regulated by the width regulating member 706 are conveyed to the dispensing port 704 under a state in which the drugs are lined up one by one in the circumferential direction of the second rotating body 703. Therefore, in the variable cassette 41B, the drugs contained in the drug containing portion 701 can be dispensed in units of one pill, and the dispensing amount of the drugs can be controlled.

As described above, when the variable cassette 41B is used, the height h1 to be regulated by the height regulating member 705 and the width w1 to be regulated by the width regulating member 706 can be changed, and therefore any type of drug can be dispensed in units of one pill.

As illustrated in FIG. 6, each variable cassette 41B includes a display 707. Content of display of the display 707 can be changed. The display 707 is electronic paper in which, when content of display is written through energization, the content of display is kept being displayed even in a non-energized state.

[Manual Dispensing Unit 43]

The manual dispensing unit 43 is used for dispensing drugs that are not suitable for dispensing from the drug cassettes 41, such as half pills or one-quarter pills, which are less than one pill. The manual dispensing unit 43 is arranged in a manner in which the manual dispensing unit 43 can be pulled out of the drug dispensing devices 4. The manual dispensing unit 43 is also used for dispensing drugs that are not contained in the drug cassettes 41.

The manual dispensing unit 43 includes a drug palette 431 and an individual dispensing portion 432 arranged below the drug palette 431. The manual dispensing unit 43 is also referred to as "detachable table adapter (DTA)". FIG. 10 is a schematic plan view of the drug palette 431 viewed from above. The drug palette 431 includes a plurality of DTA cells 431A arranged in matrix (lattice). In each DTA cell 431A, the drugs corresponding to the drug information included as prescription drugs in the prescription data are placed in units of the time of administration. The individual dispensing portion 432 can sequentially dispense the drugs placed on the drug palette 431 in units of the DTA cells 431A. A manual dispensing unit that can dispense drugs in units of the DTA cells 431A in the same manner as in the manual dispensing unit 43 is disclosed in, for example, JP 2006-110386 A.

For example, in the drug palette 431, the bottom surface of each of the DTA cells 431A can be opened and closed. In the drug palette 431, the drug placed in each of the DTA cells 431A drops toward the individual dispensing portion 432 by opening the bottom surface of each of the DTA cells 431A by predetermined driving means, for example, a motor.

The individual dispensing portion 432 includes a plurality of dispensing cells each corresponding to a position below a DTA cell 431A of the drug palette 431 under a state in which the drug palette 431 is contained in the drug dispensing device 4. The individual dispensing portion 432 includes an opening and closing mechanism that can sequentially open and close the bottom surface of each of the dispensing cells. The drugs placed in each of the dispensing cells are dispensed in order to the rotation unit 44 in units of the dispensing cells by opening the bottom surface of each of the dispensing cells in a specific order determined in advance by the opening and closing mechanism.

[Rotation Unit 44]

The rotation unit 44 includes a plurality of drug rotation portions 441, a unit rotation portion 442, and a drug discharging portion 443. The unit rotation portion 442 is rotatably supported by a base portion (not shown).

Each of the drug rotation portions 441 can alter the orientation of the drugs by rotating one pill of drug supplied from the drug cassette 41 or the manual dispensing unit 43. The unit rotation portion 442 includes six of the drug rotation portions 441 arranged about a predetermined rotation axis at intervals of 60 degrees. The unit rotation portion 442 can rotate the drug rotation portions 441 about the predetermined rotation axis.

In the drug dispensing device 4, after one drug dispensed from the drug cassette 41 drops to a drug rotation portion 441, or one drug dispensed from the manual dispensing unit 43 drops to a drug rotation portion 441, the drug rotation portions 441 are rotated and moved in order toward a position corresponding to the drug discharging portion 443.

After that, the drug placed on the drug rotation portion 441 drops to the packaging unit 45 from the drug rotation portion 441 moved to a position corresponding to the drug discharging portion 443, and is placed in a drug package 451 in the packaging unit 45.

[Packaging Unit 45]

The packaging unit 45 is configured to put the drugs supplied from one or both of the drug cassettes 41 of the drug supply unit 502 and the manual dispensing unit 43 in one packaging paper sheet in a package unit, for example, a time of administration. The packaging unit 45 forms the drug package 451 by packaging drugs in the package units with a transparent or translucent roll-shaped drug package sheet 900 and sealing the drug package sheet 900 by welding or the like. As a result, the drug package sheet 900 in which the drugs are contained in each of the drug packages 451 in the package units is discharged from the packaging unit 45. FIG. 11 is a diagram for illustrating an example of the drug package sheet 900 discharged from the packaging unit 45. As illustrated in FIG. 11, a plurality of drug packages 451 in which a plurality of drugs are packaged in the package units are continuously formed in the drug package sheet 900, and a perforated line 452 (perforations) for easily separating each of the drug packages 451 is formed between the drug packages 451.

[Packaging Control Unit 503]

As illustrated in FIG. 2, the packaging control unit 503 includes a controller 560, a storage 570, and an operation display 580. The packaging control unit 503 is configured to control the drug supply unit 502 in order to cause the drug dispensing device 4 to execute a packaging operation. The packaging control unit 503 is built in the drug dispensing device 4. The controller 510 and the controller 560 may be configured as one controller.

The controller 560 is control means including a CPU, a RAM, a ROM, an EEPROM, and the like. The controller 560 is configured to execute various types of processing by the CPU in accordance with various types of programs stored in advance in storage means such as the ROM, the EEPROM, or the storage 570. The RAM and the EEPROM are used as a temporary storage memory (working area) for various types of processing to be executed by the CPU. The controller 560 may be an integrated circuit including an ASIC or a DSP.

Specifically, the controller 560 includes a display processor 561 and a drive controller 562. More specifically, the controller 560 functions as the display processor 561 and the drive controller 562 by executing various types of processing in accordance with the control program. The display processor 561 and the drive controller 562 may be configured as electric circuits.

The display processor 561 is configured to display on display means, such as the operation display 580 or the display 530, a guidance screen for assisting the user in placing the drugs into the manual dispensing unit 43. The details are described later, but for example, the number of pills to be placed and the position in each DTA cell 431A arranged in the manual dispensing unit 43 are displayed on the guidance screen for each drug to be dispensed included as a prescription drug in the prescription data. The controller 510 may also have the function of the display processor 561, and in this case, the guidance screen is displayed on the display 530 or the operation display 580 by the controller 510.

The drive controller 562 is configured to drive the variable cassettes 41B in accordance with a driving condition set in advance so as to correspond to the drug information allocated to the variable cassettes 41B or the mounting portions 42B by the allocation processor 511, and to execute processing for dispensing the drugs corresponding to the plurality of pieces of prescription data from those variable cassette 41B. The controller 510 may also have the function of the drive controller 562.

The storage 570 is storage means for storing various types of data, such as a hard disk drive (HDD) or a solid state drive (SSD). Specifically, the storage 570 stores in advance a control program for causing a computer, for example, the controller 560, to execute packaging control processing described later (see right side of FIG. 12). The control program is recorded in a computer-readable recording medium such as a CD, a DVD, or a semiconductor memory. The control program is read from the recording medium by a reading device, for example, a disk drive (not shown), and installed in the storage 520. The present invention can be understood as an invention of the computer-readable recording medium having the above-mentioned control program recorded thereon.

The operation display 580 is operation display means including a liquid crystal monitor configured to display various types of information and operation screens in accordance with control instructions from the controller 510 or the controller 560, and a touch panel that can receive a touch operation of the user. Specifically, the operation display 580 is used to display the guidance screen for guiding the placement of drugs in the manual dispensing unit 43.

[Barcode Reader 504]

The bar code reader 504 can read a code for identifying a drug based on a JAN code, an RSS code, or a QR code written on a container (box, bottle, and the like) or a PTP sheet of the drug arranged on a drug shelf of a pharmacy. The barcode reader 504 is also used for reading the code information indicating the prescription identification information printed on the drug package 451. The information read by the barcode reader 504 is input from the barcode reader 504 to the prescription control unit 501 by wireless communication. The barcode reader 504 is, for example, a portable terminal such as a PDA or a smartphone. For example, in the drug dispensing device 4, the barcode reader 504 is used to verify the drugs taken from the drug shelf with the prescription drugs included in the prescription data.

[Prescription Control Processing and Packaging Control Processing]

Figure 12:
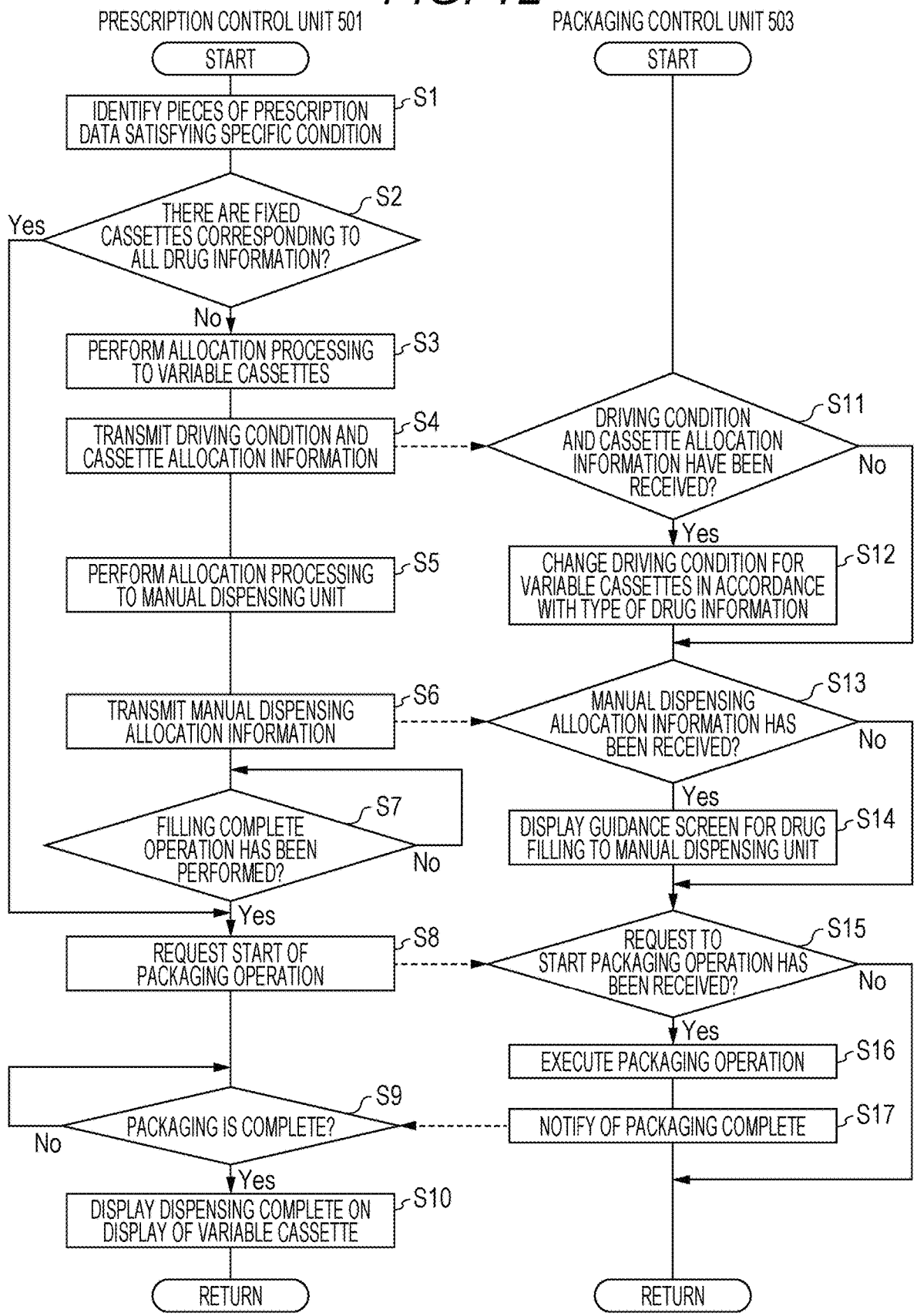
FIG. 12 is a flowchart for illustrating an example of prescription control processing and packaging control processing to be executed by the drug dispensing device according to an embodiment of the present invention.

An example of the procedure of the prescription control processing to be executed by the controller 510 of the prescription control unit 501 and the packaging control processing to be executed by the controller 560 of the packaging control unit 503 in the drug dispensing device 4 are now described with reference to FIG. 12. The present invention can be understood as an invention of a method of controlling the drug dispensing device 4, which is executed by the controller 510 and the 560. It is also possible for any one of the controller 510 and the controller 560 to execute a series of procedures for obtaining a processing result similar to the processing results of the prescription control processing and the packaging control processing.

<Prescription Control Unit 501 Side: Step S1>

First, in Step S1, the controller 510 identifies, as the prescription data to be processed, pieces of prescription data satisfying a specific condition set in advance for the prescription data input to the drug dispensing device 4. That is, in Step S1, a plurality of pieces of the prescription data may be identified as the prescription data to be processed. The prescription data identified here may be hereinafter referred to as "target prescription data".

When there is no prescription data satisfying the specific condition that has been input, the controller 510 may wait for the input of the prescription data satisfying the specific condition in Step S1. However, even in this case, when a waiting time set in advance has elapsed from input of the prescription data until the specific condition is satisfied, or when the user quits the operation, the controller 510 may determine that the specific condition is satisfied.

The specific condition includes one or a plurality of conditions. Of the prescription data input to the drug dispensing device 4, one or a plurality of pieces of the prescription data until it is determined that any one of the conditions is satisfied is identified as the target prescription data in order of earliest input or in order of earliest prescription period. The controller 510 can also set in advance whether or not each of the one or plurality of conditions is valid or invalid in response to a user operation.

Specifically, the specific condition may include a condition in which the number of pieces of the prescription data has reached a number that allows the drugs included in that prescription data as prescription drugs to be dispensed in a single placement operation using the manual dispensing unit 43. That is, the number of pieces of the prescription data in which the total number of packages of the prescription data of one or a plurality of patients is within the number of DTA cells 431A of the drug palette 431 of the manual dispensing unit 43 is identified as the target prescription data. For example, when the number of DTA cells 431A is 63, and when one piece of the prescription data is for one day's worth divided into three times daily (in the morning, around the noon, and in the evening), three DTA cells 431A are used for each piece of the prescription data. Therefore, a maximum of 21 pieces of the prescription data are identified as the target prescription data. Further, when the number of the DTA cells 431A to be used is insufficient for the number of pieces of the prescription data that has been input, a number of pieces of the prescription data for which the number of the DTA cells 431A to be used is not insufficient is identified as the target prescription data. For example, when the number of the DTA cells 431A is 63, and when one piece of the prescription data is for four days' worth divided into three times daily (in the morning, around the noon, and in the evening), 12 DTA cells 431A are used for each piece of the prescription data. Therefore, a maximum of 5 pieces of the prescription data are identified as the target prescription data. Even when the usage method is different for each piece of the prescription data, as the number of pieces of the prescription data, the controller 510 identifies a number in which the total number of packages of the prescription data is within the number of DTA cells 431A of the drug palette 431 of the manual dispensing unit 43 based on usage method of each piece of the prescription data.

In this embodiment, there is described as an example a case in which it is determined whether or not there is a fixed cassette 41A corresponding to all the drug information input as drug information indicating the types of drugs to be dispensed for the target prescription data in Step S2, which is described later. Meanwhile, the controller 510 may determine, in Step S1, based on the target prescription data and the cassette master 524, among pieces of drug information on the drugs included as prescription drugs in the prescription data input to the drug dispensing device 4, whether or not the specific condition is satisfied for drug information in which there is no corresponding fixed cassette 41A. Specifically, among pieces of drug information on the drugs included as prescription drugs in the prescription data, when drug information in which there is no corresponding fixed cassette 41A has been allocated to the manual dispensing unit 43, the controller 510 may identify, as the target prescription data, the number of pieces of the prescription data that can be dispensed in one placement operation. In this case, the specific condition is not determined to be satisfied unless the prescription data including the drug information in which there is no corresponding fixed cassette 41A is input to the drug dispensing device 4. Further, among pieces of drug information, even when there is a corresponding fixed cassette 41A, drug information in which a drug remaining amount of the fixed cassette 41A is equal to or less than a threshold remaining amount (zero or dispensing amount) set in advance may be handled in the same manner as in drug information in which there is no corresponding fixed cassette 41A. The drug remaining amount for each of the fixed cassettes 41A may be calculated based on, for example, the drug amount input when the fixed cassettes 41A are filled and on a dispensing number from the fixed cassettes 41A.

The specific condition may include a condition that the ward of the patient corresponding to the prescription data is different. Thus, for example, when the ward of the patient corresponding to the first to third pieces of prescription data input to the drug dispensing device 4 is "2F West" and the ward of the patient corresponding to the fourth piece of prescription data is "3F East", the pieces of prescription data to the third piece are identified as the target prescription data.

In addition, the specific condition may also include a condition that the doctor in charge of the patient is different, a condition that the usage method is different, a condition that outpatient/hospitalized type is different, a condition that a predetermined time has elapsed since input of the first or last piece of prescription data, or a condition that the number of pieces of the prescription data has reached a maximum number set in advance. Further, the controller 510 may also identify one or a plurality of pieces of the prescription data freely selected by a user operation as the target prescription data.

<Prescription Control Unit 501 Side: Step S2>

Next, in Step S2, the controller 510 determines whether or not the fixed cassettes 41A corresponding to all drug information input as drug information indicating the types of the drugs to be dispensed exist for the target prescription data. Specifically, the controller 510 determines, based on the cassette master 524 stored in the storage 520, whether or not a drug in which there is no corresponding fixed cassette 41A is included in the target prescription data as a prescription drug. When it is determined that there is no fixed cassette 41A corresponding to the drug information on at least one of the dispensing targets (No in Step S2), the controller 510 advances the processing to Step S3.

Meanwhile, when it is determined that the fixed cassettes 41A corresponding to the drug information on all of the dispensing targets exist (Yes in Step S2), the controller 510 advances the processing to Step S8. In this case, in Step S8, a request to start the packaging operation using each of the fixed cassettes 41A is transmitted to the controller 560, and the controller 560 executes processing for executing the packaging operation. In the case of a configuration in which the drug dispensing device 4 does not include the fixed cassettes 41A, the processing of Step S2 may be omitted, and the controller 510 may advance the processing to Step S3 after Step S1.

In the drug dispensing device 4, in response to a user operation, the controller 510 may also set any one or a plurality of the variable cassettes 41B as an immobilized cassette to be used for dispensing a drug set in advance in the same manner as in the fixed cassettes 41A. In this case, in Step S2, it may be determined whether or not the fixed cassettes 41A or the immobilization cassettes corresponding to all of the drug information exist. The cassettes set as immobilization cassettes among the variable cassettes 41B may be hereinafter referred to as "immobilization cassettes 41C".

As another embodiment, in Step S1 and Step S2, when drug information in which there is no corresponding fixed cassette 41A has been allocated to the manual dispensing unit 43, the controller 510 may identify, among the prescription data input to the drug dispensing device 4, in order of earliest input or in order of earliest prescription period, as the target prescription data, pieces of prescription data that can be dispensed in one placement operation by using the manual dispensing unit 43.

<Prescription Control Unit 501 Side: Step S3>

In Step S3, the controller 510 allocates, based on the one or plurality of pieces of target prescription data identified in Step S1, drug information on the drugs to be dispensed included in the target prescription data in which there is no corresponding fixed cassette 41A to an unallocated variable cassette 41B to which drug information has not yet been allocated. Specifically, when a plurality of pieces of prescription data are identified as the target prescription data in Step S1, drug information on the drugs to be dispensed included in the plurality of pieces of target prescription data can be allocated to the variable cassettes 41B based on the plurality of pieces of target prescription data. More specifically, in Step S3, drug information on the drugs to be dispensed in the plurality of pieces of prescription data is allocated in units of the plurality of pieces of target prescription data to the variable cassettes 41B in accordance with an allocation rule set in advance. The processing of Step S3 is an example of an allocation step to be executed by the allocation processor 511 of the controller 510. In this embodiment, as an example, there is described a case in which the drug information is allocated to the variable cassettes 41B, but the drug information may be allocated to the mounting portions 42B. In other words, in the processing of Step S3, one or a plurality of drugs to be dispensed by using the variable cassettes 41B among the drugs included in the plurality of pieces of prescription data as dispensing targets are identified in accordance with the allocation rule, and the variable cassettes 41B or the mounting portions 42B to be used for dispensing those drugs are selected and associated.

In the storage 520, cassette allocation information 521 indicating an allocation state of the variable cassettes 41B and the drug information is stored. In Step S3, the cassette allocation information 521 is updated in accordance with details of allocation of the drug information to the variable cassettes 41B. As shown in FIG. 13, in the cassette allocation information 521, a drug name or a drug ID indicating the type of drug currently allocated to each variable cassette 41B is stored as drug information. A total number of pills to be dispensed of the drug information is also stored in the cassette allocation information 521. Drug information such as a drug code or a JAN code (or RSS code) may also be stored in the cassette allocation information 521 as the drug information. Pieces of cassette identification information C1, C2, . . . are set in advance as the cassette identification information in each of the variable cassettes 41B. The cassette identification information is also stored in the RFID tag 427A of each variable cassette 41B. For variable cassettes 41B to which drug information is not currently allocated, information indicating that those variable cassettes 41B are unallocated is stored in the cassette allocation information 521. Specifically, in the cassette allocation information 521 shown in FIG. 13, pieces of drug information on the drug names "Drug M1", "Drug M2", "Drug M3", "Drug M4", and "Drug M5" are allocated to the pieces of cassette identification information "C1", "C2", "C3", "C4", and "C8" of the variable cassettes 41B, respectively. Meanwhile, in the pieces of cassette identification information "C5", "C6", and "C7", a symbol "-" indicates that drug information has not been allocated yet. The data structure of the cassette allocation information 521 shown in FIG. 13 is merely an example, and the cassette allocation information 521 may be stored in the storage 520 as one item of the medicine master, for example. In this case, the cassette identification information on the variable cassettes 41B allocated to the drugs is stored in association with each drug included in the medicine master.

Specifically, the allocation rule includes a first rule of preferentially allocating to the variable cassettes 41B drug information in which, among the pieces of drug information on the dispensing targets included in the plurality of pieces of target prescription data, a total number of pills to be dispensed is large in the plurality of pieces of target prescription data. The controller 510 performs the determination by giving preference to the first rule, and allocates the drug information included in the target prescription data to the variable cassettes 41B in accordance with the first rule. In other words, drugs having a large number of pills to be dispensed in the plurality of pieces of target prescription data are preferentially selected as the drugs using the variable cassettes 41B.

The allocation rule also includes a second rule of preferentially allocating to the variable cassettes 41B drug information in which, among the pieces of drug information on the dispensing targets included in the plurality of pieces of target prescription data, a number of pills to be dispensed in the time-of-administration unit in accordance with the usage method is unequal in the plurality of pieces of target prescription data. The controller 510 allocates the drug information to the variable cassettes 41B in accordance with the first rule, and when whether to allocate the drug information can no longer be determined based on the first rule, allocates the drug information to the variable cassettes 41B in accordance with the second rule. In other words, drugs having an unequal number of pills to be dispensed in the time-of-administration unit in accordance with the usage method in the plurality of pieces of target prescription data are preferentially selected as a drug to use a variable cassette 41B.

The allocation rule also includes a third rule of preferentially allocating to the variable cassettes 41B drug information in which, among the pieces of drug information on the dispensing targets included in the plurality of pieces of target prescription data, a number of packages is large in the plurality of pieces of target prescription data. The controller 510 allocates the drug information to the variable cassettes 41B in accordance with the first rule and the second rule, and when whether to allocate the drug information can no longer be determined in accordance with the first rule and the second rule, allocates the drug information to the variable cassettes 41B in accordance with the third rule. In other words, drugs having a large number of packages in the plurality of pieces of target prescription data are preferentially selected as a drug to use a variable cassette 41B. That is, the controller 510 preferentially executes allocation to the variable cassettes 41B in order of the first rule, the second rule, and the third rule. As another embodiment, the allocation rule may include a fourth rule of preferentially allocating to the variable cassettes 41B the drug information in order of the drug code in the plurality of pieces of target prescription data among the pieces of drug information on the dispensing targets included in the plurality of pieces of target prescription data.

As yet another embodiment, the drug information may be allocated to the variable cassettes 41B in accordance with any one or two of the first rule, the second rule, and the third rule determined in advance. The controller 510 can freely switch the validity/invalidity of each of the first rule, the second rule, and the third rule in response to a user operation. The controller 510 can also freely set the application order of the first rule, the second rule, and the third rule in response to a user operation. As yet another embodiment, even when there are unallocated variable cassettes 41B and the drug information is to be allocated to the variable cassettes 41B in accordance with the allocation rule, among the pieces of drug information, drug information having a total number of pills to be dispensed equal to or less than a specific number set in advance may not be allocated to the variable cassettes 41B. Information on whether or not each piece of drug information can use the variable cassettes 41B may be registered in the medicine master. In this case, drug information that is not usable by a variable cassette 41B is excluded from allocation to the variable cassettes 41B.

There is now described, as shown in FIG. 14, the result of allocation processing in accordance with the allocation condition when three pieces of prescription data corresponding to three patients are identified as the target prescription data. Each piece of prescription data described here is one day's worth of prescription data. It is assumed that three variable cassettes 41B having pieces of cassette identification information "C5" to "C7" among the variable cassettes 41B are unallocated cassettes to which current drug information can be allocated.

Specifically, in the example shown in FIG. 14, the prescription data having the ID "001" indicates that two pills of each of the drugs having the drug names "Drug A", "Drug B", and "Drug C" are prescribed three times daily, namely, in the morning, around the noon, and in the evening. That is, in the prescription data having the ID "001", the dispensing number for each drug is 6 pills. Similarly, the prescription data having the ID "002" indicates that two pills of each of the drugs having the drug names "Drug A" and "Drug D" are prescribed three times daily, namely, in the morning, around the noon, and in the evening, and one pill of the drug having the drug name "Drug E" is prescribed three times daily, namely, in the morning, around the noon, and in the evening. The prescription data having the ID "003" indicates that two pills of each of drugs having the drug names "Drug A", "Drug B", and "Drug D" are prescribed three times daily, namely, in the morning, around the noon, and in the evening.

In this case, in the three pieces of target prescription data, the total number of pills to be dispensed of "Drug A" is 18 pills, the total number of pills to be dispensed of "Drug B" is 12 pills, the total number of pills to be dispensed of "Drug C" is 6 pills, the total number of pills to be dispensed of "Drug D" is 12 pills, and the total number of pills to be dispensed of "Drug E" is 3 pills. Therefore, in Step S3, as shown in FIG. 15, based on the first rule, "Drug A" having the largest total number of pills to be dispensed and "Drug B" and "Drug D" having the next largest total number of pills to be dispensed are allocated to the variable cassettes 41B of "C5", "C6", and "C7", respectively, and the cassette allocation information 521 is updated. Specifically, in the cassette allocation information 521, the drug information on "Drug A", "Drug B", and "Drug D" and total numbers of pills to dispensed of "18 pills", "12 pills", and "12 pills" are allocated to the variable cassettes 41B having pieces of cassette identification information "C5", "C6", and "C7", respectively. That is, regarding the three pieces of target prescription data, drugs of the same type are allocated to the same variable cassette 41B, and in the packaging operation based on the three pieces of target prescription data, the drugs are dispensed from the same variable cassette 41B.

Meanwhile, the drug information on "Drug C" and "Drug E" is not allocated to the variable cassettes 41B, but is allocated to the manual dispensing unit 43 in Step S5 described later. Specifically, the storage 520 stores manual dispensing allocation information 523 indicating a correspondence relationship between each DTA cell 431A of the drug palette 431 of the manual dispensing unit 43 and the drug information and placement number to be placed in the DTA cells 431A. The manual dispensing allocation information 523 is updated when the drug information is allocated to the manual dispensing unit 43. Specifically, as shown in FIG. 16, in the manual dispensing allocation information 523, two pills of "Drug C" are allocated to each of the DTA cells 431A corresponding to "1A", "2A", and "3A" in the drug palette 431, and one pill of "Drug E" is allocated to each of the DTA cells 431A corresponding to "4A", "5A", and "6A".

Next, there is described an example of the allocation result obtained when other prescription data shown in FIG. 17 and FIG. 18 is identified as the target prescription data. In the example shown in FIG. 17, the prescription data having the ID "001" indicates that two pills of each of the drugs having the drug names "Drug A", "Drug B", and "Drug C" are prescribed three times daily, namely, in the morning, around the noon, and in the evening. Further, the prescription data having the ID "002" indicates that two pills of the drug having the drug name "Drug A" are prescribed three times daily, namely, in the morning, around the noon, and in the evening, and one pill of the drug having the drug name "Drug E" is prescribed three times daily, namely, in the morning, around the noon, and in the evening. The prescription data having the ID "002" also indicates that one pill of the drug having the drug name "Drug C" is prescribed twice daily, namely, in the morning and around the noon. In addition, the prescription data having the ID "003" indicates that two pills of each of drugs having the drug names "Drug A", "Drug B", and "Drug D" are prescribed three times daily, namely, in the morning, around the noon, and in the evening, and that one pill of the drug having the drug name "Drug C" is prescribed once daily, namely, in the evening.

In this case, in the three pieces of target prescription data, the total number of pills to be dispensed of "Drug A" is 18 pills, the total number of pills to be dispensed of "Drug B" is 12 pills, the total number of pills to be dispensed of "Drug C" is 6 pills, the total number of pills to be dispensed of "Drug D" is 6 pills, and the total number of pills to be dispensed of "Drug E" is 3 pills. Therefore, based on the first rule, "Drug A" having the largest total number of pills to be dispensed and "Drug B" having the next largest total number of pills to be dispensed are allocated to the variable cassettes 41B. Meanwhile, "Drug C" and "Drug D" having the next largest total number of pills to be dispensed have the same total number of pills to be dispensed, but based on the first rule, any one of "Drug C" and "Drug D" cannot be allocated to the variable cassettes 41B. Therefore, in accordance with the second rule, "Drug C" having an unequal number of pills to be dispensed in the time-of-administration unit is allocated to a variable cassette 41B. In this case, "Drug E" is allocated to the manual dispensing unit 43, and is not allocated to a variable cassette 41B.

In the example shown in FIG. 18, the prescription data having the ID "001" indicates that two pills of each of the drugs having the drug names "Drug A" and "Drug B" are prescribed three times daily, namely, in the morning, around the noon, and in the evening. Further, the prescription data having the ID "001" indicates that one pill of the drug having the drug name "Drug C" is prescribed three times daily, namely, in the morning, around the noon, and in the evening. Similarly, the prescription data having the ID "002" indicates that two pills of the drug having the drug name "Drug A" are prescribed three times daily, namely, in the morning, around the noon, and in the evening, and one pill of the each of the drugs having the drug names "Drug C" and "Drug E" are prescribed three times daily, namely, in the morning, around the noon, and in the evening. The prescription data having the ID "003" indicates that two pills of each of drugs having the drug names "Drug A", "Drug B", and "Drug D" are prescribed three times daily, namely, in the morning, around the noon, and in the evening.

In this case, in the three pieces of target prescription data, the total number of pills to be dispensed of "Drug A" is 18 pills, the total number of pills to be dispensed of "Drug B" is 12 pills, the total number of pills to be dispensed of "Drug C" is 6 pills, the total number of pills to be dispensed of "Drug D" is 6 pills, and the total number of pills to be dispensed of "Drug E" is 3 pills. Therefore, based on the first rule, "Drug A" having the largest total number of pills to be dispensed and "Drug B" having the next largest total number of pills to be dispensed are allocated to the variable cassettes 41B. Meanwhile, "Drug C" and "Drug D" having the next largest total number of pills to be dispensed have the same total number of pills to be dispensed and the same dispensing pill number for each time of administration, and hence based on the first rule and the second rule, any one of "Drug C" and "Drug D" cannot be allocated to the variable cassettes 41B. Therefore, in accordance with the third rule, "Drug C" having a larger number of packages in the plurality of pieces of target prescription data is allocated to a variable cassette 41B. In this case, "Drug E" is allocated to the manual dispensing unit 43, and is not allocated to a variable cassette 41B.

<Prescription Control Unit 501 Side: Step S4>

In Step S4, the controller 510 transmits to the controller 560 the driving condition and the cassette allocation information 521 corresponding to the target drug information on the dispensing targets allocated to the variable cassettes 41B in Step S3. As a result, the controller 560 can drive the variable cassettes 41B in accordance with the driving condition. The controller 560 can also grasp the correspondence relationship among the variable cassettes 41B, the drug information, and the total numbers of pills to dispensed based on the cassette allocation information 521. The driving condition is transmitted together with the drug information corresponding to the driving condition, but the driving condition may be transmitted in association with the cassette identification information on the variable cassettes 41B to be driven by the driving condition.

Specifically, the storage 520 stores drive correspondence information 522 indicating the correspondence relationship between the drug information and the driving condition of the variable cassettes 41B. The controller 510 identifies the driving condition corresponding to the drug information based on the drive correspondence information 522 set in advance (see FIG. 19). FIG. 19 is a table for showing an example of the drive correspondence information 522.

As shown in FIG. 19, the drive correspondence information 522 stores a driving condition set in advance in association with each piece of drug information. The driving condition includes three types of conditions, namely, a pre-driving condition relating to adjustment of the variable cassettes 41B before dispensing of the drugs from the variable cassettes 41B is started, a mid-driving condition relating to drive control during dispensing of the drugs from the variable cassettes 41B, and a driving stop condition relating to driving control at the time when dispensing of the drugs from the variable cassettes 41B is stopped.

Specifically, in the example of the drive correspondence information 522 shown in FIG. 19, as the driving condition corresponding to the drugs having the drug names "M1", "M2", "M3", and "M4", information on each of the items of a height of the dispensing path, a width of the dispensing path, a dispensing speed, a first slowdown, a second slowdown, and a reverse rotation operation is stored. However, this driving condition is merely an example. For example, when the variable cassettes 41B dispense one pill of the drug at a time by vibration, a vibration frequency or amplitude of the vibration may be defined as the driving condition. The data structure of the drive correspondence information 522 shown in FIG. 19 is also merely an example, and the driving condition defined by the drive correspondence information 522 may be stored in the storage 520 as one item of the medicine master, for example.

The height of the dispensing path and the width of the dispensing path are an example of the pre-driving condition, and are the values of the height h1 and the width w1 (see FIG. 7) set in advance as values allowing one pill of the drug to be dispensed at a time from the dispensing port 704 by the second rotating body 703 of the variable cassettes 41B.

The dispensing speed is an example of the mid-driving condition, and is a rotational speed suited to each piece of drug information as the rotational speed of the second rotating body 703 at the time when the drugs are dispensed from the variable cassettes 41B. For example, in a case in which the size of the drug is small, when the rotational speed of the drive motor 424 is high, an excessive amount of the drug tends to be dispensed before the drive motor 424 stops. Meanwhile, in a case in which the size of the drug is large, even when the rotational speed of the drive motor 424 is high, the drug is not excessively dispensed before the drive motor 424 stops. Therefore, for example, the dispensing speed of the drug set as the driving condition, that is, the dispensing speed of the drug by the second rotating body 703, may vary depending on the size of the drug. Specifically, the dispensing speed at the time when the drug size is large may be set to a lower value than the dispensing speed at the time when the drug size is small.

The first slowdown and the second slowdown are examples of the driving stop condition, and are information on a timing to execute a slowdown for gradually reducing the rotational speed of the second rotating body 703 when the dispensing of the drug from the variable cassettes 41B is stopped.

The reverse rotation operation item is an example of the driving stop condition, and is information on whether or not a reverse rotation operation is to be executed to switch the conveyance direction of the drug by the second rotating body 703 to the reverse direction when the dispensing of the drug from the variable cassettes 41B is stopped.

<Packaging Control Unit 503 Side: Step S11>

Meanwhile, in the packaging control unit 503, in Step S11, the controller 560 determines whether or not the driving condition has been received from the controller 510. When the driving condition has been received (Yes in Step S11), the controller 560 advances the processing to Step S12, and when the driving condition has not been received (No in Step S11), the controller 560 advances the processing to Step S13. The controller 560 stores the driving condition received from the controller 510 in the storage 570 in association with the cassette identification information on the variable cassette 41B to which the drug information corresponding to the driving condition is allocated. Further, the controller 560 stores the cassette allocation information 521 received together with the driving condition from the controller 510 in the storage 570.

<Packaging Control Unit 503 Side: Step S12>

In Step S12, the controller 560 drives the variable cassette 41B corresponding to the cassette identification information received together with the driving condition in accordance with the pre-driving condition of the driving condition to change the height h1 of the dispensing path and the width w1 of the dispensing path. In this way, in the drug dispensing device 4, when the pre-driving condition is included in the driving condition, the controller 560 drives the variable cassettes 41B in accordance with the pre-driving condition (height h1 and width w1 of dispensing path) to cause the drugs to be dispensed from the variable cassettes 41B, and executes the packaging operation of packaging the drugs into the drug package 451 for each time of administration (Step S16).

Specifically, the controller 560 controls the height adjustment portion 705A and the width adjustment portion 706A in accordance with the driving condition such that the type of the drugs that can be dispensed in units of one pill from the variable cassettes 41B is changed to the drugs indicated by the drug information allocated in Step S3. First, the controller 560 drives the drive motor 425 and the drive motor 426 such that the positions of the height regulating member 705 and the width regulating member 706 are returned to an initial state. The controller 560 then drives the height adjustment portion 705A by the drive motor 425, and changes the height h1 to be regulated by the height regulating member 705 of the variable cassettes 41B to the height of the dispensing path defined by the driving condition. The controller 560 also drives the width adjustment portion 706A by the drive motor 426, and changes the width w1 to be regulated by the width regulating member 706 of the variable cassette 41B to the width of the dispensing path defined by the driving condition. It is to be understood that, in a configuration in which the current state of the height regulating member 705 and the width regulating member 706 is detectable, those members are not required to be returned to their initial states.

When the height h1 and the width w1 of the dispensing path are changed in accordance with the driving condition in this manner, the variable cassettes 41B can dispense the drugs indicated by the drug information allocated in Step S3 in units of one pill, and as a result, the dispensing amount of the drugs can be controlled.

As another embodiment, the driving condition does not include the pre-driving condition, and the height h1 and the width w1 of the dispensing path can be freely adjusted by manually operating the height adjustment portion 705A and the width adjustment portion 706A of the variable cassettes 41B.

In Step S4, the controller 510 displays, based on the cassette allocation information 521, the drug information allocated to the variable cassette 41B and the total number of pills to be dispensed of the drug information on the display 707 of the variable cassette 41B to which the drug information is allocated in Step S3. In Step S12, the controller 560 may also display the drug information allocated to the variable cassette 41B and the total number of pills to be dispensed of the drug information on the display 707 based on the cassette allocation information 521.

<Prescription Control Unit 501 Side: Step S5>

In Step S5, the controller 510 allocates to the manual dispensing unit 43, among the pieces of drug information included in the one or plurality of pieces of target prescription data, one or plurality of pieces of drug information in which there is no corresponding fixed cassette 41A and that has not been allocated to the variable cassettes 41B. As a result, the drugs corresponding to the drug information that has not been allocated to the variable cassettes 41B are dispensed from the manual dispensing unit 43. The processing of Step S6 is executed by the allocation processor 511 of the controller 510. In addition, among the pieces of drug information included in the one or plurality of pieces of target prescription data, when all of the pieces of drug information in which there is no corresponding fixed cassette 41A have been allocated to the variable cassettes 41B, allocation to the manual dispensing unit 43 is not performed.

As another embodiment, after the controller 510 has allocated the drug information determined in Step S2 not to have a corresponding fixed cassette 41A to the manual dispensing unit 43, in Step S5, among that drug information, the controller 510 may cancel the allocation to the manual dispensing unit 43 of the drug information allocated to the variable cassettes 41B in Step S3. Specifically, in Step S5, after the drug information has been stored in the manual dispensing allocation information 523 in association with each DTA cell 431A of the manual dispensing unit 43, the controller 510 may delete the drug information allocated to the variable cassettes 41B from the manual dispensing allocation information 523. At this time, there may arise a situation in which, in the manual dispensing allocation information 523, among those DTA cells 431A, drug information is not allocated to the DTA cells 431A from which the corresponding drug information has been deleted. However, the controller 510 may be configured not to change the correspondence relationship between the drug information allocated in Step S5 and the DTA cells 431A. With this configuration, there is no deviation in the relationship between the position and usage method of each DTA cell 431A in the drug palette 431, and human error in the placement operation of the drugs may be suppressed. Meanwhile, when there is no longer any drug information corresponding to the DTA cell 431A due to the allocation of the drug information to the variable cassettes 41B, the manual dispensing allocation information 523 may be updated to fill in the allocation state between each of the DTA cells 431A and the drug information. In this case, it is possible to perform the packaging operation for a larger amount of prescription data at one time by using the DTA cells 431A that have become available.

<Prescription Control Unit 501 Side: Step S6>

In Step S6, the controller 510 transmits the drug information on the dispensing targets allocated to the manual dispensing unit 43 in Step S5 to the controller 560. As a result, the controller 560 can grasp details of the usage of the manual dispensing unit 43 during execution of the packaging operation for the target prescription data.

<Packaging Control Unit 503 Side: Step S13>

Meanwhile, in the packaging control unit 503, the controller 560 determines whether or not the manual dispensing allocation information 523 indicating details of the allocation from the controller 510 to the manual dispensing unit 43 has been received in Step S13. When the manual dispensing allocation information 523 has been received (Yes in Step S13), the controller 560 advances the processing to Step S14, and when the manual dispensing allocation information 523 has not been received (No in Step S13), the controller 560 advances the processing to Step S15.

<Packaging Control Unit 503 Side: Step S14>

In Step S14, the control 560 displays, based on the manual dispensing allocation information 523, on the operation display 580 a guidance screen providing guidance regarding the drugs to be filled into each of the DTA cells 431A. The processing of Step S14 is executed by the display processor 561. The processing of Step S14 may also be executed by the controller 510.

FIG. 20 to FIG. 23 are each a diagram for illustrating an example of the guidance screen. As illustrated in FIG. 20, the guidance screen includes an area A1 for showing a list of the drug information allocated to the manual dispensing unit 43 in the manual dispensing allocation information 523, and an area A2 for showing the placement position and the number of drugs to be placed of the drug corresponding to the drug information currently selected among pieces of drug information shown in the area A1. The controller 560 also displays in the area A1, among the pieces of drug information allocated to the manual dispensing unit 43 in the manual dispensing allocation information 52, the drug information for which the placement position and the number of drugs to be placed have been displayed in the area A2 and the drug information for which the placement position and the number of drugs to be placed have not yet been displayed in the area A2, in an identifiable manner based on a character color, a background color, or the like.

Specifically, at the start of displaying the guidance screen, the controller 560 selects in the area A2 the drug information displayed at the top in the area A1, as illustrated in FIG. 20, and displays the placement position and number of drugs to be placed corresponding to that drug information. More specifically, in the example illustrated in FIG. 20, guidance for showing that two pills of drug C are to be placed into each of "1A" to "3A" of the DTA cells 431A is provided.

Figure 21:
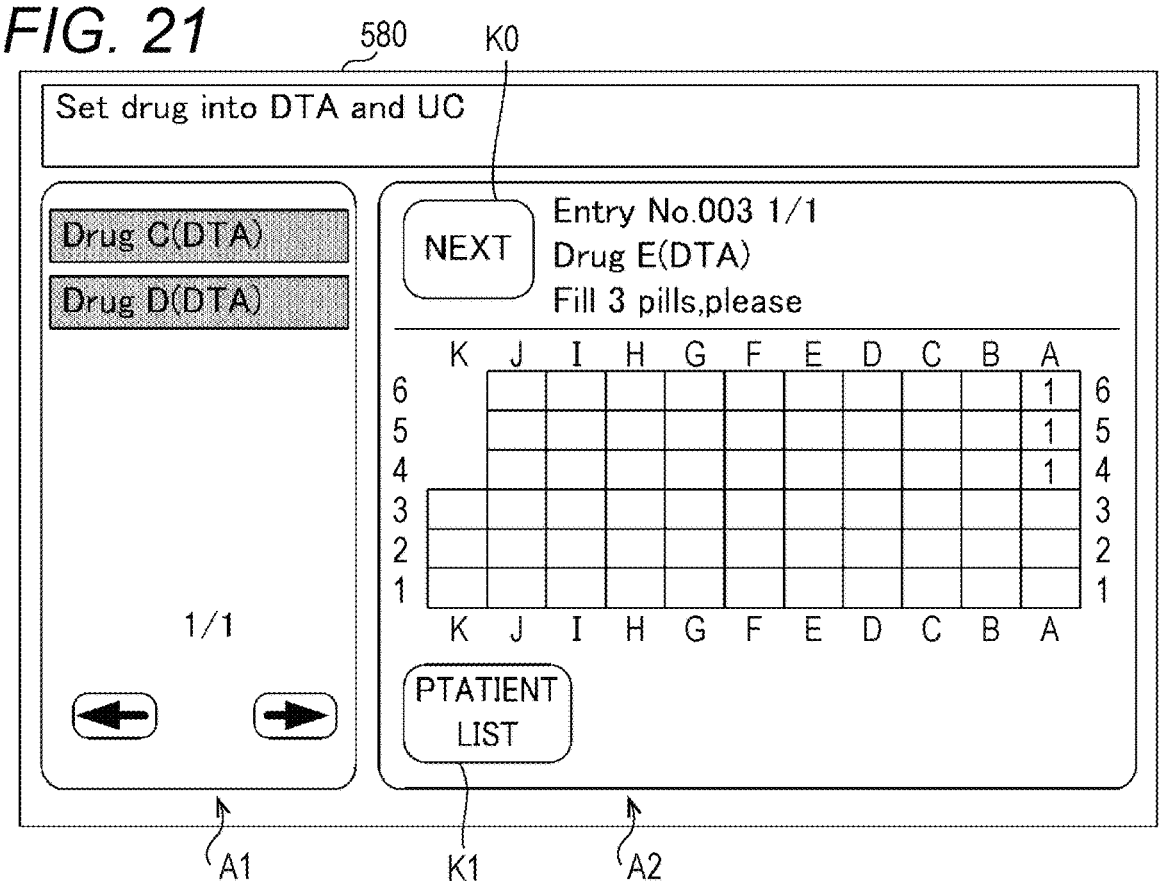
FIG. 21 is a diagram for illustrating an example of a display screen displayed by the drug dispensing system in an embodiment of the present invention.

Then, when an operation key K0 displayed on the guidance screen is operated, the controller 560 selects the drug information one below the currently displayed drug information displayed in that area, as illustrated in FIG. 21, and displays the placement position and the number of drugs to be placed of the drug corresponding to that drug information in the area A2. Specifically, in the example illustrated in FIG. 21, guidance for showing that one pill of drug E is to be placed in each of "4A" to "6A" of the DTA cells 431A is provided. Even when drug information is selected in the area A1, the controller 560 displays the placement position and the number of placements corresponding to the selected drug information in the area A2.

Figure 22:
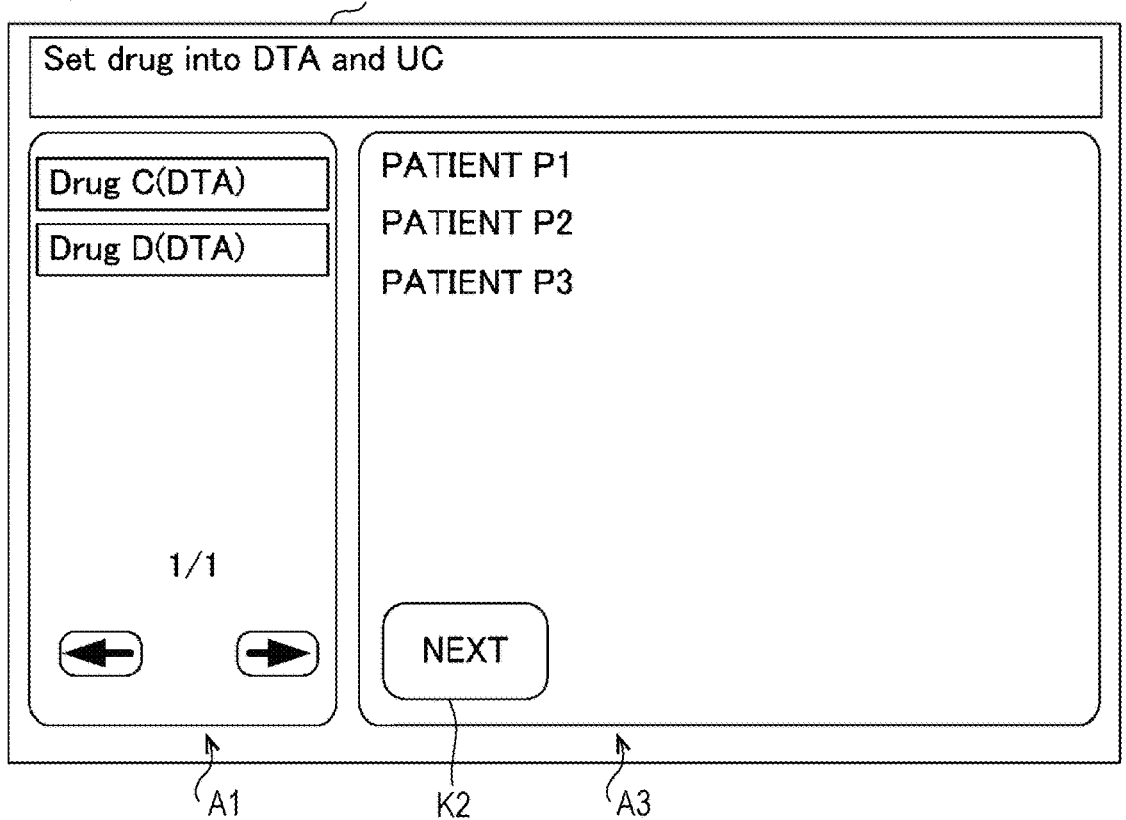
FIG. 22 is a diagram for illustrating an example of a display screen displayed by the drug dispensing system in an embodiment of the present invention.
Figure 23:
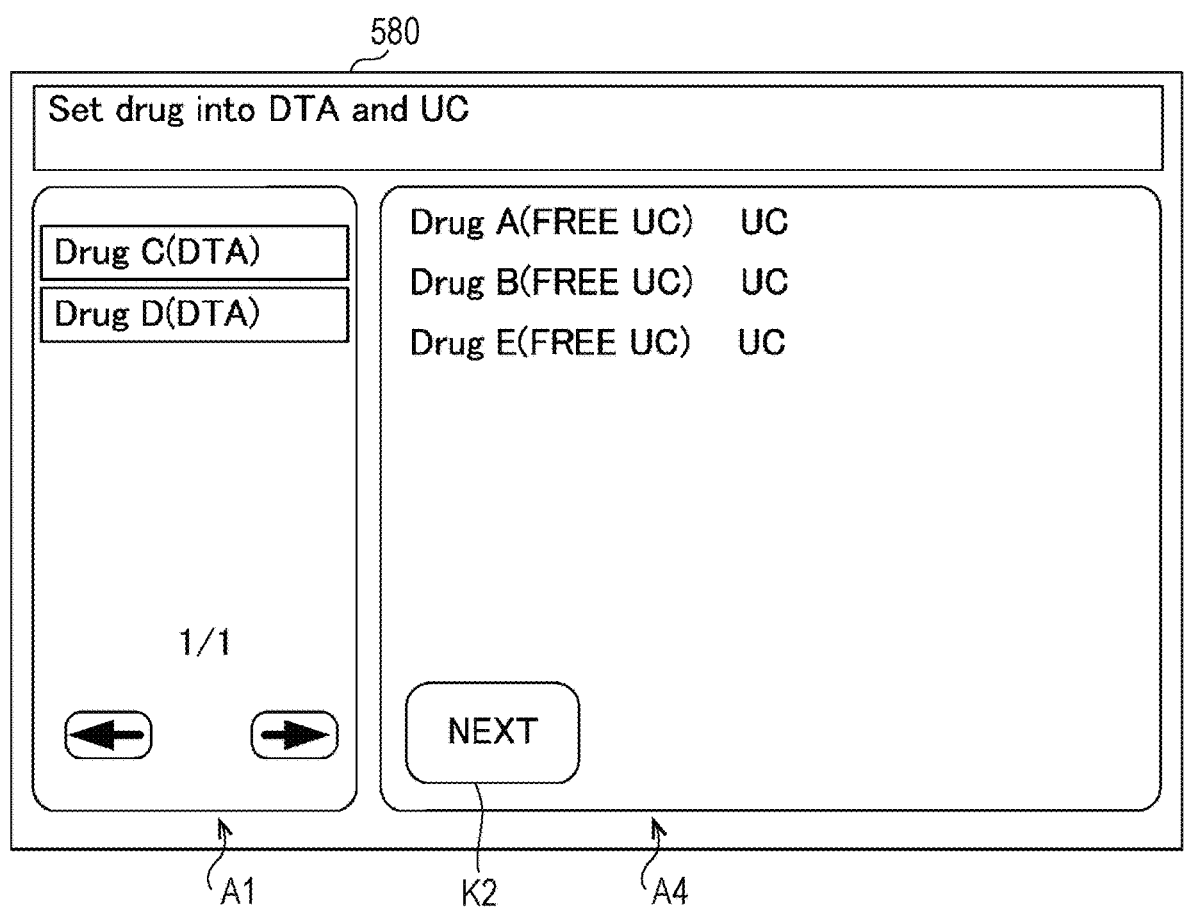
FIG. 23 is a diagram for illustrating an example of a display screen displayed by the drug dispensing system in an embodiment of the present invention.

When an operation key K1 displayed on the guidance screen is operated, the controller 560 displays in an area A3 of the operation display 580 a list of patients corresponding to the current target prescription data, as illustrated in FIG. 22. When an operation key K2 displayed on the operation display 580 is operated under a state in which the list of patients is displayed, the controller 560 displays a list of the drug information allocated to the variable cassettes 41B among the pieces of drug information included as prescription drugs in the current target prescription data. In the example illustrated in FIG. 23, "UC" representing an abbreviation of the variable cassettes 41B is displayed in association with the drugs allocated to the variable set 41B. In this case as well, a list of the drug information allocated to the manual dispensing unit 43 among pieces of drug information included as prescription drugs in the current target prescription data is displayed in the area A1. Therefore, the user can easily grasp the allocation destination of the drug information included as prescription drugs in the current target prescription data by referring to the display of the operation display 580. As another embodiment, for the drug information in which there is a corresponding fixed cassette 41A or an immobilized cassette 41C among the pieces of drug information included as prescription drugs in the current target prescription data, a correspondence relationship between the fixed cassette 41A or immobilized cassette 41C and the drug information may be displayed in an area A4. Further, when the operation key K2 is operated under a state in which a list of drug information allocated to the variable cassettes 41B is displayed, for example, the screen may return to the screen on which the list of patients is displayed.

<Prescription Control Unit 501 Side: Step S7>

Then, in Step S7, the controller 510 determines whether or not a filling complete operation indicating that filling of the drugs to a variable cassette 41B is complete has been performed on the operation device 540. Specifically, when the drug information has been allocated to a variable cassette 41B in Step S3 and the drug information has been displayed on the display 707 of the variable cassette 41B, the user removes the variable cassette 41B from the drug supply unit 502. Then, the user places the required number of pills of the drug into the variable cassette 41B while referring to the prescription corresponding to the prescription data or the information displayed on the display 707. The user then mounts the variable cassette 41B to the drug supply unit 502 and performs the filling complete operation on the operation device 540. When the drug information is also allocated to the manual dispensing unit 43 in Step S5, the user opens the drug palette 431 of the manual dispensing unit 43, places the drug, closes the drug palette 431, and then performs the filling complete operation. The mounting/dismounting of the variable cassette 41B and the opening/closing of the manual dispensing unit 43 may be an example of the filling complete operation.

Until the filling complete operation is performed (No in Step S7), the controller 510 waits for the processing in Step S7. Meanwhile, when it is determined that the filling complete operation has been performed (Yes in Step S7), the controller 510 advances the processing to Step S8. When a plurality of pieces of drug information has been allocated to a plurality of the variable cassettes 41B in Step S3, in Step S7, it is determined whether or not the drug filling complete operation has been performed for all the variable cassettes 41B corresponding to the pieces of drug information. Further, when the drug information is allocated to the manual dispensing unit 43 in Step S5, in Step S7, it may be determined whether or not the opening/closing operation of the drug palette 431 of the manual dispensing unit 43 is complete.

<Prescription Control Unit 501 Side: Step S8 and Step S9>

In Step S8, the controller 510 transmits to the controller 560 a request to start the packaging operation based on each of the pieces of target prescription data. Then, in Step S9, the controller 510 waits for a packaging operation completion notification from the controller 560 (No in Step S9). When the packaging operation completion notification is received (Yes in Step S9), the controller 510 advances the processing to Step S10.

<Prescription Control Unit 501 Side: Step S10>

In Step S10, the controller 510 displays a message indicating that dispensing is complete on the display 707 of the variable cassettes 41B for which dispensing has been completed. For example, in Step S9, the words "dispensing complete" may be displayed on the display 707, or the display of the drug information on the display 707 may be deleted.

<Packaging Control Unit 503 Side: Step S15>

Meanwhile, in the packaging control unit 503, in Step S15, the controller 560 determines whether or not a request to start the packaging operation from the controller 510 has been received. When a request to start the packaging operation has been received (Yes in Step S15), the controller 560 advances the processing to Step S16, and when a request to start the packaging operation has not been received (No in Step S15), the controller 560 advances the processing to Step S11.

<Packaging Control Unit 503 Side: Step S16>

In Step S16, the controller 560 executes the packaging operation based on the one or plurality of pieces of target prescription data in accordance with the request to start the packaging operation. Specifically, the controller 560 dispenses the required drugs from the fixed cassettes 41A, the variable cassettes 41B, and the manual dispensing unit 43 of the drug supply unit 502 based on the one or plurality of pieces of target prescription data. Then, the controller 560 causes the packaging unit 45 to package the drugs dispensed from the fixed cassettes 41A, the variable cassettes 41B, and the manual dispensing unit 43 in package units, for example, the time of administration. Step S16 is an example of a driving step to be executed by the drive controller 562 of the controller 560. In the packaging operation, the number of drugs dispensed from the variable cassettes 41B is counted by a counter including an optical sensor (not shown), which is arranged in the dispensing port 704 of the variable cassettes 41B, and is input to the controller 560 as the dispensing number. As a result, the controller 560 can control the driving of the variable cassettes 41B based on the dispensing number input from the counter, and can dispense only a dispensing amount (prescription amount) set in advance from the variable cassettes 41B.

When there are a plurality of pieces of the target prescription data, the packaging operation is sequentially executed on each of the plurality of pieces of target prescription data. At this time, when the drug information on the drugs included as dispensing targets in a plurality of pieces of target prescription data is allocated to the same variable cassette 41B, in the packaging operation corresponding to the plurality of pieces of target prescription data, the same drug is dispensed from the same variable cassette 41B. As a result, the efficiency of the filling operation by the user is increased because the user is not required to fill the same drug into a plurality of the variable cassettes 41B or to repeatedly fill the same drug into the variable cassettes 41B, and can collectively fill the drug into one variable cassette 41B. In contrast, when the same drug included in each of the pieces of prescription data is allocated to different variable cassettes 41B, or when the same drug included in each of the pieces of prescription data is repeatedly allocated to the same variable cassette 41B, the efficiency of the filling operation by the user is decreased because the user is required to fill the same drug into a plurality of the variable cassettes 41B or to repeatedly fill the same drug into the variable cassettes 41B.

<Packaging Control Unit 503 Side: Step S17>

After that, when the packaging operation corresponding to the one or plurality of pieces of target prescription data is complete in Step S14, in the subsequent Step S17, the controller 560 transmits a packaging operation completion notification to the controller 510.

As described above, in the drug dispensing device 4, based on a plurality of pieces of prescription data, the drug information on the one or plurality of drugs to be dispensed included in the plurality of pieces of prescription data is allocated to the variable cassettes 41B. Therefore, the variable cassettes 41B can be used more efficiently than in the case in which the drug information is allocated to the variable cassettes 41B based on individual pieces of prescription data.

In this embodiment, as an example, there is described a case in which the drug information is allocated to the variable cassettes 41B. However, the controller 510 may allocate the drug information to the mounting portions 42B to which the variable cassettes 41B are mounted in place of the variable cassettes 41B. In this case, in Step S4, the controller 510 transmits information indicating a correspondence relationship between the drug information and the mounting portions 42B to the controller 560 together with the driving condition corresponding to the drug information on the dispensing targets. As a result, the controller 560 can drive the variable cassettes 41B mounted to the mounting portions 42B in accordance with the driving condition.

[Pill Supplement Control Function]

In the drug dispensing device 4, when there are not enough pills in the fixed cassettes 41A or the immobilized cassettes 41C with respect to the required dispensing amount, the pills cannot be dispensed, and hence the operation is halted. Therefore, the user may supplement the pills in advance when the remaining amount of the pills in the fixed cassettes 41A or the immobilized cassettes 41C becomes smaller. However, when the pills are supplemented before the pills in the fixed cassettes 41A or the immobilized cassettes 41C run out, there may be a mixture of old and new pills, and previously stored pills may be dispensed later than more newly stored pills. However, for example, when a plurality of fixed cassettes 41A or immobilized cassettes 41C are arranged for one type of pill, control can be performed such that the pills are dispensed from the plurality of fixed cassettes 41A or immobilized cassettes 41C in the order in which the pills have been supplemented. In this way, it is possible to implement first-in first-out of the pills that can be dispensed earlier than the pill supplemented later, but this also requires an increase in the number of fixed cassettes 41A or immobilized cassettes 41C.

In contrast, the drug dispensing device 4 has a pill supplement control function that can reduce the frequency of pill shortages and implement first-in-first-out of the pills while suppressing an increase in the number of fixed cassettes 41A or immobilized cassettes 41C. The pill supplement control function is now described. In the drug dispensing device 4, as described above, pills are dispensed based on a plurality of pieces of prescription data satisfying the specific condition. However, the drug dispensing device 4 may also be configured to dispense pills based on one piece of prescription data.

FIG. 24 is a flowchart for illustrating an example of pill supplement processing to be executed by the controller 510 in order to implement the pill supplement control function. The controller 560 may execute the pill supplement processing, or the controller 510 and the controller 560 may execute the pill supplement processing in cooperation. FIG. 25A is a table for showing an example of the cassette allocation information 521, and FIG. 25B is a table for showing an example of the cassette master 524. FIG. 26 is a flowchart for illustrating an example of pill dispensing processing to be executed by the controller 560 as a part of the packaging operation of Step S16 (see FIG. 12).

[Pill Supplement Processing]

First, the pill supplement processing to be executed by the controller 510 is described with reference to FIG. 24.

<Step S21>

In step S21, the controller 510 determines whether or not to start pill supplement. When it is determined to start pill supplement (Step S21: Yes), the processing advances to Step S22. When it is determined not to start pill supplement (Step S21: No), the processing advances to Step S291.

For example, the controller 510 identifies pills corresponding to the drug information as the supplement object and determines to start pill supplement when a selection operation of the drug information on the pill to be supplemented and an operation of requesting to start pill supplement are performed on the operation device 540. When the remaining amount of pills of a fixed cassette 41A or an immobilized cassette 41C is equal to or less than a preset threshold value, the controller 510 may also identify those pills to be the supplement object, and automatically determine to start pill supplement.

<Step S22>

In Step S22, the controller 510 identifies the drug cassette 41 to serve as the supplement destination of the pills determined to be supplemented in Step S21.

Specifically, the controller 510 displays on the display 530 a display screen for prompting the user to select any one of the fixed cassettes 41A and the variable cassettes 41B as a candidate for the supplement destination of the pills. The controller 510 identifies any one of the fixed cassettes 41A and the variable cassettes 41B as the supplement destination of the pill in accordance with a user operation on the display screen. For example, when the fixed cassettes 41A are selected, the controller 510 identifies the fixed cassette 41A corresponding to the supplement object pills as the supplement destination based on the cassette master 524. When a specific variable cassette 41B is selected, the controller 510 identifies the variable cassette 41B as the supplement destination and updates the cassette allocation information 521 such that the selected variable cassette 41B is set as an immobilized cassette 41C. When a user operation for automatically identifying any variable cassette 41B as the supplement destination of the pills is performed, the controller 510 may identify, as the supplement destination of the pills, an unallocated variable cassette 41B to which drug information is yet to be allocated based on the cassette allocation information 521, and update the cassette allocation information 521 such that the identified variable cassette 41B is set as the immobilized cassette 41C. Further, as described above, in this embodiment, there is described as an example a case in which the drug information is allocated to the variable cassettes 41B, but the drug information may be allocated to the mounting portions 42B.

<Step S23>

In Step S23, the controller 510 displays on the display 530 supplement-related information, such as the drug information on the pills identified as the supplement object in Step S21 and the cassette identification information on the drug cassette 41 identified as the supplement destination in Step S22. When the supplement destination of the pills is a variable cassette 41B, the controller 510 may display the supplement-related information on the display 707 of the variable cassette 41B.

<Step S24>

In Step S24, the controller 510 determines whether or not the drug cassette 41 identified in Step S22 as the supplement destination of the pills is a variable cassette 41B. When the drug cassette 41 is a variable cassette 41B (Step S24: Yes), the processing advances to Step S25. When the drug cassette 41 identified in Step S22 as the supplement destination of the pills is not a variable cassette 41B (Step S24: No), the processing advances to Step S26.

<Step S25>

In Step S25, the controller 510 transmits to the controller 560 the driving condition corresponding to the drug information on the pills identified as the supplement object in Step S21 and the cassette identification information on the variable cassette 41B of the supplement destination identified in Step S22. When the drug information is to be allocated to a mounting portion 42B, the identification information on the mounting portion 42B is transmitted in place of the cassette identification information. As a result, the controller 560 can drive the variable cassette 41B identified in Step S22 in accordance with the driving condition (Step S11 and Step S12 of FIG. 12).

<Step S26>

In Step S26, the controller 510 determines whether or not a supplement complete operation indicating that the supplement of the drug for the drug cassette 41 of the supplement destination is complete has been performed on the operation device 540. In the processing of this step, the controller 510 waits until the supplement complete operation is performed (Step S26: No). When it is determined that the supplement complete operation has been performed (Step S26: Yes), the processing advances to Step S27.

<Step S27>

In Step S27, the controller 510 receives information such as the number of pills to be supplemented into the drug cassette 41 of the supplement destination in accordance with a user operation, updates inventory information on the pills stored in the storage 520 based on the information, and advances the processing to Step S28. For example, when the number of pills to be supplemented to the drug cassette 41 has been input, the controller 510 increases the inventory of those pills in the inventory information by the input number of pills to be supplemented. In addition, the inventory information is transmitted from the controller 510 to the controller 560 after the update of Step S27, and is also stored in the storage 570 by the controller 560. Similarly, even when the inventory information is updated by the controller 560, the inventory information is transmitted from the controller 560 to the controller 510 and stored in the storage 520 by the controller 510. That is, the inventory information in the storage 520 and the storage 570 are synchronized. The number of the pills to be supplemented may also be input when the drug information on the pills to be supplemented is selected in Step S21. The inventory information may be included in the cassette allocation information 521 and the cassette master 524, and the cassette allocation information 521 or the cassette master 524 may be transmitted and received as required.

<Step S28>

In Step S28, the controller 510 executes processing for recording the supplement day and time for the drug cassette 41 this time. The supplement day and time is a day and time determined in Step S21 at which the supplement is to be started, or the day and time determined in Step 27 at which the supplement is completed (execution start day and time of Step S28), for example. The controller 510 has a clock function for calculating the current time or a function for acquiring the current time from an external device.

Specifically, when the supplement destination is an immobilized cassette 41C, the controller 510 records the supplement day and time in association with the immobilized cassette 41C in the cassette allocation information 521. FIG. 25A is a table for showing an example of the cassette allocation information 521. In the cassette allocation information 521 shown in FIG. 25A, the variable cassettes 41B having pieces of cassette identification information "C1", "C2", "C3", and "C4" are set as the immobilized cassettes 41C corresponding to the pills having pieces of drug information "Drug M1", "Drug M2", "Drug M3", and "Drug M3", respectively. Meanwhile, in the cassette allocation information 521, pieces of drug information on "Drug A" and "Drug B" and the total numbers of pills to dispensed "18 pills" and "12 pills" are allocated to the variable cassettes 41B having pieces of cassette identification information "C5" and "C6", respectively. In the cassette allocation information 521, for the variable cassettes 41B set as the immobilized cassettes 41C, for example, "Fix" indicating that the cassette is an immobilized cassette is recorded together with the drug information. As shown in FIG. 25A, the cassette allocation information 521 stores the supplement day and time in association with the cassette identification information and the drug information.

Meanwhile, when the supplement destination is a fixed cassette 41A, the controller 510 records the supplement day and time in association with the fixed cassette 41A in the cassette master 524. FIG. 25B is a table for showing an example of the cassette master 524. In the cassette master 524 shown in FIG. 25B, the fixed cassettes 41A having pieces of cassette identification information "C11", "C12", "C13", "C14", "C15", "C16", "C17", and "C18" are set as the fixed cassettes 41A corresponding to the pills having pieces of drug information "Drug M1", "Drug M2", "Drug M3", "Drug M4", "Drug M5", "Drug M6", "Drug M7", and "Drug M1", respectively. As shown in FIG. 25B, the cassette master 524 stores the supplement day and time in association with the cassette identification information and the drug information. For example, in the example shown in FIG.

25A and FIG. 25B, for "Drug M1", it can be seen that the supplement day and time (11:23 on Jan. 2, 2017) of the fixed cassette 41A having the cassette identification information "C11" is the earliest, the supplement day and time (11:23 on Jan. 3, 2017) of the immobilized cassette 41C having the cassette identification information "C1" is the next earliest, and the supplement day and time (11:30 on Jan. 9, 2017) of the fixed cassette 41A having the cassette identification information "C18" is the next earliest.

<Step S29>

In Step S29, the controller 510 transmits the cassette allocation information 521 and the cassette master 524 to the controller 560. As a result, the controller 560 that has received the cassette allocation information 521 and the cassette master 524 stores the cassette allocation information 521 and the cassette master 524 in the storage 570. More specifically, the cassette allocation information 521 and the cassette master 524 stored in the storage 570 are updated to the latest information. Therefore, the controller 560 can grasp the supplement day and time of the pills to each of the drug cassettes 41 based on the cassette allocation information 521 and the cassette master 524. The controller 510 may transmit, among the cassette allocation information 521 and the cassette master 524, only the information updated in Step S28 to the controller 560.

<Step S291>

In Step S291, the controller 510 determines whether or not shortage notification information has been received from the controller 560. As described later, when a pill runs out in any of the drug cassettes 41, the controller 560 transmits the shortage notification information to the controller 510 (FIG. 26: Step S342). When it is determined that a shortage notification has been received (Step S291: Yes), the processing advances to Step S292, and when it is determined that a shortage notification has not been received (Step S291: No), the processing returns to Step S21.

<Step S292>

In Step S292, the controller 510 updates the cassette allocation information 521 or the cassette master 524 based on the shortage notification information. Specifically, the controller 510 refers to cassette identification information indicating the drug cassette 41 that has run out included in the shortage notification information, and deletes the information on the supplement day and time for the drug cassette 41 corresponding to the cassette identification information.

For example, when the drug cassette 41 that has run out is a fixed cassette 41A, the information on the supplement day and time of the fixed cassette 41A corresponding to the cassette identification information in the cassette master 524 is deleted. The controller 510 may delete the information on the supplement day and time in the cassette master 524 not only in the case of the pill supplement processing, but also when an operation for removing pills from the fixed cassette 41A is performed.

Meanwhile, when the drug cassette 41 that has run out is an immobilized cassette 41C, in the cassette allocation information 521, the information on the supplement day and time of the immobilized cassette 41C corresponding to the cassette identification information and the drug information allocated to the immobilized cassette 41C are deleted. Specifically, the allocation state of the drug information to the immobilized cassette 41C is released, and the immobilized cassette 41C returns to a state in which the immobilized cassette 41C is usable as a variable cassette 41B. The controller 510 may also delete the information on the supplement day and time of the immobilized cassette 41C and the drug information allocated to the immobilized cassette 41C not only in the case of the pill supplement processing, but also at any timing when an operation for removing pills from the immobilized cassette 41C is performed or when an operation for releasing the allocation of the drug information to the immobilized cassette 41C (operation for returning to a variable cassette 41B).

<Step S293>

In Step S293, the controller 510 transmits the cassette allocation information 521 and the cassette master 524 to the controller 560. As a result, the controller 560 that has received the cassette allocation information 521 and the cassette master 524 stores the cassette allocation information 521 and the cassette master 524 in the storage 570. That is, the cassette allocation information 521 and the cassette master 524 stored in the storage 570 are updated to the latest information. The controller 510 may transmit, among the cassette allocation information 521 and the cassette master 524, only the information updated in Step S292 to the controller 560.

[Pill Dispensing Processing]

The pill dispensing processing to be executed as a part of the packaging operation in Step S16 (see FIG. 12) by the controller 560 is now described with reference to FIG. 26.

<Step S31>

In Step S31, the controller 560 identifies, based on the target prescription data, the cassette allocation information 521, and the cassette master 524, the drug cassette 41 to dispense the prescription drug included in the target prescription data, as a dispensing source.

Specifically, the controller 560 refers to the cassette allocation information 521 and the cassette master 524, and identifies as the dispensing source the drug cassette 41 having the earliest supplement day and time among the drug cassettes 41 to which the prescription drugs included in the target prescription data are allocated. For example, in the example shown in FIG. 25A and FIG. 25B, when the drug information on the prescription drug is "Drug M1", among the drug cassettes 41 having the pieces of cassette identification information allocated to the same drug information, namely, "C1", "C11", and "C18", the fixed cassette 41A "C11" having the earliest supplement day and time is identified as the dispensing source.

<Step S32>

In Step S32, the controller 560 sequentially starts, based on each piece of the target prescription data, the packaging operation of dispensing the pills from each of the drug cassettes 41 identified in Step S31 and packaging the pills into each time of administration. The controller 560 decreases the remaining amount of those pills in the inventory information stored in the storage 570 by the dispensing amount each time dispensing of the pills is complete for one piece of target prescription data, for example, and transmits the inventory information to the controller 510. However, the update timing and transmission timing of the inventory information are not limited to the above-mentioned timing.

<Step S33>

In Step S33, the controller 560 determines whether or not any of the drug cassettes 41 used in the packaging operation has run out of pills. Specifically, when a pill is not dispensed even after a predetermined time has elapsed after the drug cassette 41 starts to be driven, the controller 560 determines that the drug cassette 41 has run out of pills. The controller 560 may also update the inventory information stored in the storage 570 each time a pill is dispensed from the drug cassette 41, and determine whether or not the drug cassettes 41 have run out of pills based on the inventory information. When it is determined that the pills have run out (Step S33:

Yes), the processing advances to Step S34, and when it is determined that the pills have not run out (Step S33: No), the processing advances to Step S35.

<Step S34>

In Step S34, the controller 560 determines, based on the cassette allocation information 521 and the cassette master 524, whether or not, in addition to the drug cassette 41 determined as having run out of pills in Step S33, there is a drug cassette 41 to which the same pill as the pill of that drug cassette 41 is allocated. When it is determined that there is a drug cassette 41 to which the same pill is allocated (Step S34: Yes), the processing advances to Step S31, and when it is determined that there is no drug cassette 41 to which the same pill is allocated (Step S34: No), the processing advances to Step S341.

<Step S341>

In Step S341, the controller 560 halts the packaging operation being executed in the drug dispensing device 4.

<Step S342>

In Step S342, the controller 560 executes shortage notification processing of notifying of notification information such as the drug information on the pills determined in Step S33 to have run out, and the cassette identification information on the drug cassette 41. Specifically, the controller 560 displays the notification information on the operation display 580, and transmits cassette identification information on the drug cassette 41 and information indicating that a shortage has occurred to the controller 510. Based on this, in Step S291 to Step S293, the controller 510 updates the cassette allocation information 521 or the cassette master 524 and transmits the updated information to the controller 560. In the shortage notification processing, the notification information may be transmitted to the controller 510 and displayed on the display 530 by the controller 510. Further, the shortage notification processing is not limited to a display, and the notification of shortage may be given by voice or a buzzer sound. In addition, the shortage notification may also be displayed on the display 707 of the drug cassette 41.

In Step S342, the controller 560 advances the processing to Step S35 in cases in which, for example, the cassette allocation information 521 or the cassette master 524 has been received from the controller 510, the shortage in the drug cassette 41 has been resolved, a predetermined resumption operation by the user has been performed, or the drug cassette 41 determined as having run out is dismounted, and the packaging operation is restarted in Step S32.

<Step S35>

In Step S35, the controller 560 determines whether or not the packaging operation has been completed for the target prescription data received in response to the request to start the packaging operation received in Step S16. When it is determined that the packaging operation has been completed for the target prescription data (Step S35: Yes), the pill dispensing processing ends, and the processing advances to Step S17 (see FIG. 12). When it is determined that the packaging operation has not been completed for the target prescription data (Step S35: No), the processing returns to Step S32, and the packaging operations are sequentially executed.

As described above, in the pill supplement control function, the variable cassettes 41B may be temporarily set as an immobilized cassette 41C when pills are supplemented. As a result, it is possible to reduce the frequency of pill shortages and implement first-in first-out of the pills without increasing the number of fixed cassettes 41A or immobilized cassettes 41C.

For example, the following case is considered. Specifically, the dispensing source is changed when pills of "Drug M1" are dispensed under a state in which, as shown in FIG. 25A and FIG. 25B, of the drug cassettes 41 corresponding to "Drug M1", the fixed cassette 41A having the cassette identification information "C11" has the earliest supplement day and time, the immobilized cassette 41C having the cassette identification information "C1" has the next earliest supplement day and time, and the fixed cassette 41A having the cassette identification information "C18" has the next earliest supplement day and time. In this case, first, the fixed cassette 41A having the cassette identification information "C11" is used as the dispensing source. When a shortage occurs in the fixed cassette 41A having the cassette identification information "C11", the immobilized cassette 41C having the cassette identification information "C1" is used as the dispensing source. Subsequently, when a shortage occurs in the fixed cassette 41A having the cassette identification information "C1", the fixed cassette 41A having the cassette identification information "C18" is used as the dispensing source. In addition, when pills are supplemented to the fixed cassette 41A having the cassette identification information "C11", which was used first, the supplement day and time of that fixed cassette 41A is after the supplement day and time of the fixed cassette 41A having the cassette identification information "C18". Therefore, the fixed cassette 41A having the cassette identification information "C11" is used as the dispensing source after a shortage occurs in the fixed cassette 41A having the cassette identification information "C18".

As another example, the following case is considered. Specifically, under a state in which, as shown in FIG. 25A and FIG. 25B, of the drug cassettes 41 corresponding to "Drug M2", the cassette identification information for "C12" has an earlier supplement day and time than that for "C2", after the fixed cassette 41A having the cassette identification information "C12" is used and a shortage occurs, pills are supplemented to that fixed cassette 41A. In this case, first, the fixed cassette 41A having the cassette identification information "C12" is used, then the immobilized cassette 41C having the cassette identification information "C2" is used, and when a shortage occurs in that immobilized cassette 41C, the allocation of the drug information to the immobilized cassette 41C is released. Then, the fixed cassette 41A having the cassette identification information "C12", in which pills were supplemented after the shortage occurred after the immobilized cassette 41C, is used again. That is, for the pills having drug information "Drug M2", in addition to the fixed cassette 41A having cassette identification information "C12", the variable cassette 41B having cassette identification information "C2" can also be temporarily used as an immobilized cassette 41C. In this way, a variable cassette 41B can be temporarily used as an immobilized cassette 41C corresponding to "Drug M2". After the setting of that immobilized cassette 41C is released, the variable cassette 41B can be used as a normal variable cassette 41B to dispense any type of pill, and therefore it is possible to reduce the frequency of pill shortages while suppressing an increase in the number of fixed cassettes 41A and immobilized cassettes 41C.

As another example, the following case is considered. Specifically, under a state in which, as shown in FIG. 25A and FIG. 25B, of the drug cassettes 41 corresponding to "Drug M3", the supplement day and time for the cassette identification information for "C13" is the earliest, then "C3", and then "C4", after the fixed cassette 41A having the cassette identification information "C13" is used and a shortage occurs, pills are supplemented to that fixed cassette 41A. In this case, first, the fixed cassette 41A having the cassette identification information "C13" is used, then the immobilized cassette 41C having the cassette identification information "C3" is used, and when a shortage occurs in that immobilized cassette 41C, the allocation of the drug information to the immobilized cassette 41C is released. Then, when the immobilization cassette 41C having the cassette identification information "C4" is used and a shortage occurs in the immobilization cassette 41C, the allocation of the drug information to the immobilization cassette 41C is released. Further, the fixed cassette 41A having the cassette identification information "C13", in which pills were supplemented after the shortage occurred after the immobilized cassette 41C, is used again. Specifically, for the pills having drug information "Drug M3", in addition to the fixed cassette 41A having cassette identification information "C3", the variable cassettes 41B having pieces of cassette identification information "C3" and "C4" can also be temporarily used as immobilized cassettes 41C.

In this embodiment, there is described an example in which first-in first-out of the pills is implemented by controlling the usage order of each of the drug cassettes 41 based on the supplement day and time. However, the priority of each of the drug cassettes 41 may be updated based on the supplement day and time such that first-in first-out of the pills is implemented, and the usage order of each of the drug cassettes 41 may be controlled based on the priority.

[Immobilization Recommendation Function]

As described above, in the drug dispensing device 4, the variable cassettes 41B can be set and used as an immobilized cassette 41C corresponding to a specific pill. The type of pill allocated to the variable cassette 41B to be used as an immobilized cassette 41C is selected by the user. However, the drug dispensing device 4 may have an immobilization recommendation function that can recommend the type of pill to be allocated to the variable cassette 41B.

Specifically, in the drug dispensing device 4, when a user operation for selecting the variable cassette 41B to be used as an immobilized cassette 41C is received, the controller 510 selects the type of pill (drug information) recommended to be allocated to the variable cassette 41B in accordance with a condition determined in advance, and displays the selected pill type on the display 530. The controller 510 may record information such as the number of times of being dispensed in the past through use of the manual dispensing unit 43, the amount dispensed through use of the manual dispensing unit 43 in the past, or the number of times a prescription drug has been included in the prescription data input in the past, and select the type of pill based on any one or a plurality of those pieces of information.

For example, the controller 510 selects the type of pill that has been most frequently dispensed by the manual dispensing unit 43 in the past and that can be dispensed by the variable cassettes 41B. As another example, the controller 510 selects the type of pill that has the largest amount dispensed by the manual dispensing unit 43 in the past and that can be dispensed by the variable cassettes 41B. As another example, the controller 510 selects the type of pill that has been included most frequently as a prescription drug in the prescription data input in the past. As another example, when a fixed cassette 41A or an immobilized cassette 41C corresponding to the target pill already exists, the controller 510 may be configured not to select that pill. Even when a fixed cassette 41A or an immobilized cassette 41C corresponding to the target pill already exists, in cases in which, for example, the number of times of being dispensed in the past or the amount dispensed in the past is equal to or more than a predetermined value, the controller 510 may select that pill as an exception.

SUPPLEMENTARY NOTES OF THE INVENTION

Supplementary Note 1

There is provided a drug dispensing device including: a variable cassette configured to dispense any type of drug; a mounting portion, to and from which the variable cassette is mountable and dismountable; an allocation processor configured to allocate, based on a plurality of pieces of prescription data, drug information on a drug to be dispensed included in the plurality of pieces of prescription data to the variable cassette or the mounting portion; and a drive controller configured to drive the variable cassette in accordance with a driving condition set in advance in association with the drug information allocated to the variable cassette or the mounting portion by the allocation processor, to thereby dispense from the variable cassette the drug corresponding to the plurality of pieces of prescription data.

Supplementary Note 2

In the drug dispensing device according to Supplementary Note 1, the allocation processor is configured to allocate, to the variable cassette or the mounting portion, the drug information on the drug to be dispensed included in the plurality of pieces of prescription data in accordance with an allocation rule set advance, in units of the plurality of pieces of prescription data.

Supplementary Note 3

In the drug dispensing device according to Supplementary Note 2, the allocation rule includes a first rule of preferentially allocating, to the variable cassette or the mounting portion, drug information in which, among pieces of drug information on a dispensing target included in the plurality of pieces of prescription data, a total number of pills to be dispensed is large in the plurality of pieces of prescription data.

Supplementary Note 4

In the drug dispensing device according to Supplementary Note 2, the allocation rule includes a second rule of preferentially allocating, to the variable cassette or the mounting portion, drug information in which, among pieces of drug information on a dispensing target included in the plurality of pieces of prescription data, a number of pills to be dispensed in a time-of-administration unit in accordance with a usage method is unequal in the plurality of pieces of prescription data.

Supplementary Note 5

In the drug dispensing device according to Supplementary Note 2, the allocation rule includes a third rule of preferentially allocating, to the variable cassette or the mounting portion, drug information in which, among pieces of drug information on a dispensing target included in the plurality of pieces of prescription data, a number of packages is large in the plurality of pieces of prescription data.

Supplementary Note 6

In the drug dispensing device according to Supplementary Note 2, the allocation rule includes: a first rule of preferentially allocating, to the variable cassette or the mounting portion, drug information in which, among pieces of drug information on a dispensing target included in the plurality of pieces of prescription data, a total number of pills to be dispensed is large in the plurality of pieces of prescription data; a second rule of preferentially allocating, to the variable cassette or the mounting portion, drug information in which, among pieces of drug information on a dispensing target included in the plurality of pieces of prescription data, a number of pills to be dispensed in a time-of-administration unit in accordance with a usage method is unequal in the plurality of pieces of prescription data; and a third rule of preferentially allocating, to the variable cassette or the mounting portion, drug information in which, among pieces of drug information on a dispensing target included in the plurality of pieces of prescription data, a number of packages is large in the plurality of pieces of prescription data, and the allocation processor is configured to preferentially execute the allocation to the variable cassette or the mounting portion in order of the first rule, the second rule, and the third rule.

Supplementary Note 7

In the drug dispensing device according to any one of Supplementary Notes 1 to 6, the allocation processor is configured to identify a plurality of pieces of prescription data satisfying a specific condition set in advance, and allocate, based on the identified plurality of pieces of prescription data, the drug information on a drug to be dispensed included in the plurality of pieces of prescription data to the variable cassette or the mounting portion.

Supplementary Note 8

In the drug dispensing device according to Supplementary Note 7, the drug dispensing device further includes fixed cassettes each configured to dispense a type of drug determined in advance, and the allocation processor is configured to determine whether the specific condition is satisfied based on the drug information included in the plurality of pieces of prescription data and on master information indicating drug information dispensable from each of the fixed cassettes.

Supplementary Note 9

In the drug dispensing device according to any one of Supplementary Notes 1 to 8, the drug dispensing device further includes: fixed cassettes each configured to dispense a type of drug determined in advance; and a manual dispensing unit configured to dispense drugs contained in a plurality of cells in units of the plurality of cells, and the allocation processor is configured to allocate, among pieces of drug information on a dispensing target included in the plurality of pieces of prescription data, drug information having no corresponding fixed cassette, to the variable cassette or the manual dispensing unit.

Supplementary Note 10

There is provided a control method for a drug dispensing device, the drug dispensing device including a variable cassette configured to dispense any type of drug, and a mounting portion, to and from which the variable cassette is mountable and dismountable, the control method including: an allocation step of allocating, based on a plurality of pieces of prescription data, drug information on a drug to be dispensed included in the plurality of pieces of prescription data to the variable cassette or the mounting portion; and a driving step of driving the variable cassette in accordance with a driving condition set in advance in association with the drug information allocated to the variable cassette or the mounting portion in the allocation step, to thereby dispense from the variable cassette the drug corresponding to the plurality of pieces of prescription data.

Supplementary Note 11

There is provided a control program for causing a controller of a drug dispensing device including a variable cassette configured to dispense any type of drug, and a mounting portion, to and from which the variable cassette is mountable and dismountable, to execute: an allocation step of allocating, based on a plurality of pieces of prescription data, drug information on a drug to be dispensed included in the plurality of pieces of prescription data to the variable cassette or the mounting portion; and a driving step of driving the variable cassette in accordance with a driving condition set in advance in association with the drug information allocated to the variable cassette or the mounting portion in the allocation step, to thereby dispense from the variable cassette the drug corresponding to the plurality of pieces of prescription data.

The invention claimed is:

1. A drug dispensing device, comprising:
a plurality of variable cassettes, each variable cassette configured to dispense any single type among a plurality of types of drug;
a mounting portion, to which any variable cassette is removably mountable;
an allocation processor programmed to allocate, based on a plurality of pieces of prescription data, each piece of prescription data including at least one type of drug to be dispensed among the plurality of types of drugs, drug information including one type of drug among the plurality of types of drugs to the corresponding variable cassette among the plurality of variable cassettes or to the mounting portion; and
a drive controller configured to drive the corresponding variable cassette, based on a predetermined driving condition associated with the drug information allocated by the allocation processor to the corresponding variable cassette or the mounting portion, to dispense the drug from the corresponding variable cassette;
wherein the allocation processor is programmed to allocate the drug information in accordance with a predetermined allocation rule, in units of the plurality of pieces of prescription data; and
wherein the allocation rule includes a second rule of preferentially allocating, to the corresponding variable cassette or the mounting portion, the drug information, based on a number of pills to be dispensed in a time-of-administration dosage unit being unequal to a number of pills included in a usage method included in the plurality of pieces of prescription data.

2. The drug dispensing device according to claim 1, wherein the allocation rule comprises a first rule of preferentially allocating, to the corresponding variable cassette or the mounting portion, the drug information, based on a total amount of drug to be dispensed included in the plurality of pieces of prescription data.

3. The drug dispensing device according to claim 1, wherein the allocation rule includes a third rule of preferentially allocating, to the corresponding variable cassette or the mounting portion, the drug information, based on a number of packages included in the plurality of pieces of prescription data.

4. The drug dispensing device according to claim 1, wherein the allocation rule comprises:
    a first rule of preferentially allocating, to the corresponding variable cassette or the mounting portion, the drug information, based on a total amount of drug to be dispensed included in the plurality of pieces of prescription data;
    a second rule of preferentially allocating, to the corresponding variable cassette or the mounting portion, the drug information, based on a number of pills to be dispensed in a time-of-administration dosage unit being unequal to a number of pills included in a usage method included in the plurality of pieces of prescription data; and
    a third rule of preferentially allocating, to the corresponding variable cassette or the mounting portion, the drug information, based on a number of packages included in the plurality of pieces of prescription data, and
    wherein the allocation processor is programmed to preferentially execute the allocation to the corresponding variable cassette or the mounting portion in order of the first rule, the second rule, and the third rule.

5. The drug dispensing device according to claim 1, wherein the allocation processor is further programmed to determine whether the plurality of pieces of prescription data satisfy a predetermined condition, and
    in response to a determination that the plurality of pieces of prescription data satisfy the predetermined condition, allocate, based on the plurality of pieces of prescription data, the drug information to the corresponding variable cassette or the mounting portion.

6. The drug dispensing device according to claim 5, further comprising fixed cassettes each configured to dispense a predetermined type of drug,
    wherein the allocation processor is programmed to determine whether the predetermined condition is satisfied based on
        the plurality of types of drug included in the plurality of pieces of prescription data, and
        master information indicating the predetermined type of drug dispensable from each of the fixed cassettes.

7. The drug dispensing device according to claim 1, further comprising:
    fixed cassettes each configured to dispense a predetermined type of drug; and
    a manual dispensing comprising a drug palette unit configured to dispense drugs contained in a plurality of cells of the drug palette in units of the plurality of cells,
    wherein the allocation processor is further programmed to allocate drug information having no corresponding fixed cassette, to the corresponding variable cassette or the manual dispensing unit.

8. The drug dispensing device according to claim 1, wherein each piece of prescription data among the plurality of pieces of prescription data includes a patient identifier, a drug identifier, and a dose.

* * * * *